United States Patent
Belalcazar

(10) Patent No.: US 12,016,623 B2
(45) Date of Patent: Jun. 25, 2024

(54) HIGH VOLTAGE ABLATION CATHETER SYSTEM

(71) Applicant: Hugo Andres Belalcazar, Minneapolis, MN (US)

(72) Inventor: Hugo Andres Belalcazar, Minneapolis, MN (US)

(*) Notice: Subject to any disclaimer, the term of this patent is extended or adjusted under 35 U.S.C. 154(b) by 0 days.

(21) Appl. No.: 18/233,424

(22) Filed: Aug. 14, 2023

(65) Prior Publication Data

US 2023/0380894 A1  Nov. 30, 2023

Related U.S. Application Data

(63) Continuation of application No. 17/739,094, filed on May 7, 2022, now abandoned.

(60) Provisional application No. 63/186,783, filed on May 10, 2021.

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/0022* (2013.01); *A61B 2018/00375* (2013.01); *A61B 2018/00577* (2013.01)

(58) Field of Classification Search
CPC ............ A61B 18/1206; A61B 18/1492; A61B 2018/0022; A61B 2018/00375; A61B 2018/00577
See application file for complete search history.

(56) References Cited

U.S. PATENT DOCUMENTS

| | | | |
|---|---|---|---|
| 6,546,934 B1 | 4/2003 | Ingle et al. | |
| 7,293,562 B2 | 11/2007 | Malecki et al. | |
| 8,235,986 B2 | 8/2012 | Kulesa et al. | |
| 8,295,902 B2 | 10/2012 | Salahieh et al. | |
| 8,538,555 B1 | 9/2013 | Chitre et al. | |
| 8,932,287 B2 | 1/2015 | Gelbart et al. | |
| 9,131,980 B2 | 9/2015 | Bloom | |
| 9,717,557 B2 | 8/2017 | Salahieh et al. | |
| 10,524,859 B2 | 1/2020 | Vrba et al. | |
| 10,918,438 B2 | 2/2021 | Weinkam et al. | |
| 2007/0156135 A1 | 7/2007 | Rubinsky et al. | |
| 2010/0256628 A1* | 10/2010 | Pearson | A61N 1/0519 606/41 |

(Continued)

OTHER PUBLICATIONS

Lahorte, Philipe, Authorized Officer European Patent Office, Written Opinion of the International Searching Authority, International Application No. PCT/US2022/028271, dated Nov. 14, 2023, 9 pages.

*Primary Examiner* — Thomas A Giuliani
*Assistant Examiner* — Christine A Dedoulis
(74) *Attorney, Agent, or Firm* — Krenz Patent Law, LLC

(57) ABSTRACT

A system for ablating bodily tissue of a patient includes a high-voltage electrical generator configured to provide electrical pulses of at least 500 volts, a fluid having an electrical conductivity of not more than 0.01 Siemens per meter, and an ablation catheter that includes a catheter shaft, an expandable membrane attached to the catheter shaft, and a plurality of electrodes, each electrically coupled to the high-voltage electrical generator. The fluid inflates the expandable membrane when provided to the interior space of the expandable membrane.

16 Claims, 13 Drawing Sheets

(56) References Cited

U.S. PATENT DOCUMENTS

| | | |
|---|---|---|
| 2014/0357956 A1 | 12/2014 | Salahieh et al. |
| 2016/0143522 A1 | 5/2016 | Ransbury et al. |
| 2017/0042614 A1* | 2/2017 | Salahieh ............ A61B 1/00082 |
| 2019/0231421 A1 | 8/2019 | Viswanathan et al. |
| 2020/0163707 A1 | 5/2020 | Sliwa et al. |
| 2022/0008123 A1 | 1/2022 | Altmann et al. |
| 2022/0133043 A1 | 5/2022 | Olson et al. |
| 2022/0133403 A1 | 5/2022 | Olson et al. |
| 2023/0012307 A1 | 1/2023 | Harlev et al. |
| 2023/0264031 A1 | 8/2023 | Harlev et al. |

\* cited by examiner

FIG. 9A
FIG. 9B
FIG. 9C
FIG. 9D

HIGH VOLTAGE ABLATION CATHETER SYSTEM

CROSS REFERENCE TO RELATED APPLICATION

This application is a Continuation of U.S. application Ser. No. 17/739,094, filed 7 May 2022, entitled "HIGH VOLTAGE ABLATION CATHETER SYSTEM," which claims the benefit of U.S. Provisional Patent Application No. 63/186,783, filed 10 May 2021, entitled "HIGH VOLTAGE ABLATION CATHETER," the entire contents of each of which is hereby incorporated by reference in its entirety.

TECHNICAL FIELD

This document generally describes devices, systems, and methods for ablating bodily tissue of a patient.

BACKGROUND

Ablation of cardiac tissue using electrical energy has been used to correct rhythm disorders of the heart, having been practiced in clinical electrophysiology. Conventionally, a catheter is passed percutaneously through major vessels of the body's circulatory system to reach the heart. There, electrodes are deployed to contact or come close to the cardiac tissue that is to be ablated. Electrical energy is then delivered to the tissue via the electrodes to create a lesion in the tissue. The lesion can prevent cardiac electrical activity that may sustain an arrhythmia. The creation of durable transmural lesions is a goal of ablation.

One aspect of this clinical practice involves electrical isolation of pulmonary veins, where an arrhythmia called atrial fibrillation can initiate. The pulmonary veins receive blood from the lungs into the left atrium of the heart before the blood passes to the left ventricle through the mitral valve and is pumped to the rest of the body. An ablation catheter can be used to create the lesions at an ostium or antrum of one or more pulmonary veins to prevent the conduction of cardiac electrical activity from the veins to the left atrium, and thereby electrically isolate those one or more veins from the left atrium. This procedure is known as pulmonary vein isolation, or "PVI."

One method of cardiac ablation using electrical energy involves delivering radio frequency ("RF") electrical energy to cardiac tissue. RF ablation involves applying lower-voltage electrical energy (e.g., pulses of less than 200V) to cardiac tissue, where the lower-voltage electrical energy heats the cardiac tissue. The heat can cause the desired lesion, but in some cases can also undesirably damage other nearby tissue, because such tissue may also be heated and damaged. Some ablation catheters that use RF electrical energy to ablate have used a balloon with electrodes on an outer surface of the balloon, where the balloon is inflated with saline as a fill fluid when the catheter reaches a desired ablation location. Because the voltages used with RF ablation are relatively low, electric fields generated by the RF voltages are also of relatively lower strength. Saline, the typical balloon-fill fluid used for RF ablations, is a relatively electrically conductive fluid. Another ablation technology that has used balloon catheters is cryo-ablation. One example of cryo-ablation uses extremely cold gas to inflate a balloon and freeze cardiac tissue in contact with the balloon, to create a lesion.

More recently, cardiac ablations have been performed using high voltages (e.g., over 500V) for electroporation, with which the higher voltages cause damage to cardiac tissue cells to create a lesion. Ablation catheters that have used these high voltages have used one or more electrodes on the shaft of the catheter. One example uses one or two catheter shaft tip electrodes for focal or point ablations, and another example uses a catheter having a distal circular portion with several electrodes on the circular portion. As compared to the lower voltages of RF ablation, using high voltages for electroporation can introduce new challenges, including an increased risk of electrical arcing between electrodes, which can result in a short circuit and acute catheter failure that can impart catheter fragments into the circulation, electrolytic gas generation, which can lead to a formation of gas bubbles in the blood and increased risk of stroke, and very high electrical fields that can damage tissues other than the targeted cardiac tissues.

SUMMARY

In a first general aspect, a system for ablating bodily tissue of a patient includes a high-voltage electrical generator configured to provide electrical pulses of at least 500 volts. The system also includes an ablation catheter that includes a catheter shaft and an expandable membrane, the expandable membrane attached to the catheter shaft at a distal section of the catheter shaft. The expandable membrane has an inner surface and an outer surface, and the inner surface defines an interior space of the expandable membrane. The catheter shaft includes a lumen that extends from a proximal section of the catheter shaft to an orifice that fluidly couples the lumen with the interior space of the expandable membrane. The ablation catheter further includes a plurality of electrodes disposed on the outer surface of the expandable membrane, and each electrode of the plurality of electrodes is electrically coupled to the high-voltage electrical generator by a respective electrical conductor. The system further includes a fluid having an electrical conductivity of not more than 0.01 Siemens per meter, the fluid injected into the lumen to expand the expandable membrane.

Implementations can include one or more of the following. The expandable membrane may have a thickness of not more than 200 microns, or of not more than 50 microns. A fixed volume of the fluid may be injected into the lumen to expand the expandable membrane, and the fixed volume of the fluid may remain within at least one of the interior space of the expandable membrane or the lumen for a duration of electrical energy delivery by the high-voltage electrical generator. The expandable membrane may have a thickness of not more than 50 microns, a fixed volume of the fluid may be injected into the lumen to expand the expandable membrane, and the fixed volume of the fluid may remain within at least one of the interior space of the expandable membrane or the lumen for a duration of electrical energy delivery by the high-voltage electrical generator. The fluid may be non-circulatory. The electrical pulses of at least 500 volts may be rectangular pulses. The expandable membrane may have an electrical conductivity of not more than 0.01 Siemens per meter. The fluid may be a dextrose solution of not more than 30% dextrose in water. The fluid may be D5W. The fluid may be selected from the group consisting of deionized water, nitrogen, carbon dioxide, and helium. Prior to the fluid being injected into the lumen to expand the expandable membrane, the distal section of the ablation catheter may be located at at least one of an ostium of a pulmonary vein of the patient or at an antrum of a pulmonary vein of the patient. Prior to the fluid being injected into the lumen to expand the expandable membrane, a distal portion of the ablation catheter may be located in a left atrium of the patient.

In a second general aspect, a system for ablating bodily tissue of a patient includes a high-voltage electrical generator configured to provide electrical pulses of at least 500 volts. The system also includes an ablation catheter that includes a catheter shaft and an expandable membrane, the expandable membrane attached to the catheter shaft at a distal section of the catheter shaft. The expandable membrane has an inner surface and an outer surface, and the inner surface defines an interior space of the expandable membrane. The catheter shaft includes a lumen that extends from a proximal section of the catheter shaft to an orifice that fluidly couples the lumen with the interior space of the expandable membrane. The ablation catheter also includes a plurality of flexible splines, each including an outward-facing surface and an inward-facing surface. The ablation catheter further includes a plurality of electrodes, where each electrode of the plurality of electrodes is disposed on an outward-facing surface of a flexible spline of the plurality of flexible splines. Each electrode of the plurality of electrodes is electrically coupled to the high-voltage electrical generator by a respective electrical conductor. The system further includes a fluid having an electrical conductivity of not more than 0.01 Siemens per meter, the fluid injected into the lumen to expand the expandable membrane. The outer surface of the expandable membrane contacts the inward-facing surfaces of each flexible spline of the plurality of flexible splines.

Implementations can include one or more of the following. The expandable membrane may have a thickness of not more than 200 microns, or of not more than 50 microns. A fixed volume of the fluid may be injected into the lumen to expand the expandable membrane, and the fixed volume of the fluid may remain within at least one of the interior space of the expandable membrane or the lumen for a duration of electrical energy delivery by the high-voltage electrical generator. The expandable membrane may have a thickness of not more than 50 microns, a fixed volume of the fluid may be injected into the lumen to expand the expandable membrane, and the fixed volume of the fluid may remain within at least one of the interior space of the expandable membrane or the lumen for a duration of electrical energy delivery by the high-voltage electrical generator. The fluid may be non-circulatory. The electrical pulses of at least 500 volts may be rectangular pulses. The expandable membrane may have an electrical conductivity of not more than 0.01 Siemens per meter. The fluid may be a dextrose solution of not more than 30% dextrose in water. The fluid may be D5W. The fluid may be selected from the group consisting of deionized water, nitrogen, carbon dioxide, and helium. Prior to the fluid being injected into the lumen to expand the expandable membrane, a distal portion of the ablation catheter may be located at at least one of an ostium of a pulmonary vein of the patient or at an antrum of a pulmonary vein of the patient. Prior to the fluid being injected into the lumen to expand the expandable membrane, a distal portion of the ablation catheter may be located in a left atrium of the patient.

In a third general aspect, a system for ablating bodily tissue of a patient includes a high-voltage electrical generator configured to provide electrical pulses of at least 500 volts. The system also includes an ablation catheter that includes a catheter shaft and an expandable membrane, the expandable membrane attached to the catheter shaft at a distal section of the catheter shaft. The expandable membrane has an inner surface and an outer surface, and the inner surface defines an interior space of the expandable membrane. The ablation catheter also includes a plurality of electrodes disposed on the outer surface of the expandable membrane, and each electrode of the plurality of electrodes is electrically coupled to the high-voltage electrical generator by a respective electrical conductor. The system further includes a fluid having an electrical conductivity of not more than 0.01 Siemens per meter, the fluid to inflate the expandable membrane when provided to the interior space of the expandable membrane.

In a fourth general aspect, a system for ablating bodily tissue of a patient includes a high-voltage electrical generator configured to provide electrical pulses of at least 500 volts. The system also includes an ablation catheter that includes a catheter shaft and an expandable membrane, the expandable membrane attached to the catheter shaft at a distal section of the catheter shaft. The expandable membrane has an inner surface and an outer surface, and the inner surface defines an interior space of the expandable membrane. The ablation catheter also includes a plurality of flexible splines, each including an outward-facing surface and an inward-facing surface. The ablation catheter further includes a plurality of electrodes, where each electrode of the plurality of electrodes is disposed on an outward-facing surface of a flexible spline of the plurality of flexible splines. Each electrode of the plurality of electrodes is electrically coupled to the high-voltage electrical generator by a respective electrical conductor. The system further includes a fluid having an electrical conductivity of not more than 0.01 Siemens per meter, the fluid to inflate the expandable membrane when provided to the interior space of the expandable membrane. The outer surface of the expandable membrane contacts the inward-facing surfaces of each flexible spline of the plurality of flexible splines.

BRIEF DESCRIPTION OF THE DRAWINGS

FIG. 9A is a schematic that shows an example energy delivery method for ablating bodily tissue, for an example system with sixteen electrodes.

FIG. 9B is a schematic that shows another example energy delivery method for ablating bodily tissue, for a system with fourteen electrodes.

FIG. 9C is a schematic that shows another example energy delivery method for ablating bodily tissue, for an example system with twelve electrodes.

FIG. 9D is a schematic that shows yet another example energy delivery method for ablating bodily tissue, for an example system with eight electrodes.

Like reference symbols in the various drawings indicate like elements.

DETAILED DESCRIPTION

Described herein are devices, systems, and methods that can be used to provide high-voltage, or high-current, electroporation ablation using an ablation catheter that includes a balloon or flexible membrane, and includes, as a fill fluid for the balloon or flexible membrane, a low-electrical-conductivity fluid. Advantages that may be provided by the devices, systems, and methods described herein can include minimized risk of balloon or flexible membrane rupture, even when the higher electric field strengths that can be associated with electroporation may be present, according to some implementations. Advantages may also include shorter ablation procedure durations, according to some implementations. Advantages may further include improved safety by reducing risk of damage to body tissues that are nearby the tissue targeted for the ablation, according to some implementations. Advantages may further include reduced energy use for the ablation procedure, according to some implementations. Because the devices, systems and methods discussed herein may permit high-voltage or high-current electroporation energy delivery with an ablation catheter that includes a balloon or an expandable membrane, electroporation ablation may be provided with a catheter that may better conform to irregular anatomies of a patient, such as left atrium anatomies near pulmonary veins, which may increase efficacy of lesion formation, according to some implementations. Also, ablation catheters that include a balloon or flexible membrane may be easier for a physician, especially an inexperienced physician, to place at a target location, and in some implementations the devices, systems, and methods discussed herein may permit electroporation ablation to be used with ablation catheters that include a balloon or flexible membrane.

Figure 1:
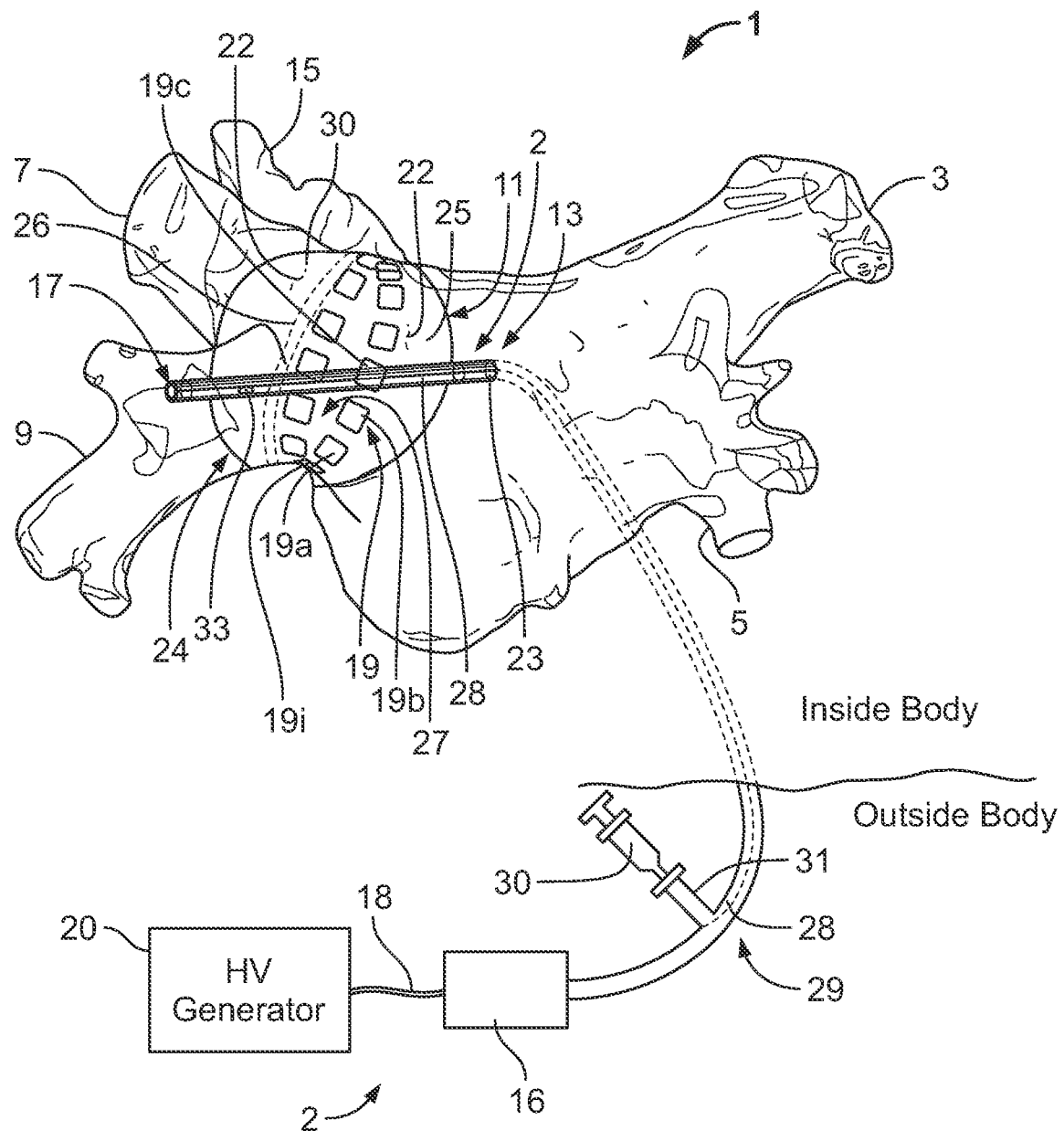
FIG. 1 is a posterior view of a left atrium of a human heart and an example system for ablating bodily tissue of a patient.

FIG. 1 shows a posterior view of a left atrium 1 of a human heart, and an example system 2 for ablating bodily tissue of a patient. A right superior pulmonary vein 3 is shown, as well as a right inferior pulmonary vein 5, a left inferior pulmonary vein 9, and a left superior pulmonary vein 7. Also shown is the left atrium appendage 15. As is well known in the field of clinical electrophysiology regarding delivery of a catheter to a desired left atrial location in preparation for an ablation, a catheter can reach the left atrium 1 by a percutaneous delivery, passing through major vessels of the circulation to reach the heart, and through a trans-septal puncture from the right atrium into the left atrium 1.

The system 2 for ablating bodily tissue includes an example ablation catheter 13, an example high-voltage electrical generator 20, and example fluid 22 having low electrical conductivity. In the example of FIG. 1, a distal end 17 of the ablation catheter 13 has been passed into the left inferior pulmonary vein 9. In some examples, a distal section 24 of the ablation catheter 13 may be located at an ostium of a pulmonary vein of a patient. In some examples, the distal section 24 of the ablation catheter 13 may be located at an antrum of a pulmonary vein of the patient. In some examples, the distal section 24 of the ablation catheter 13 may be located in the left atrium of the patient.

Ablation catheter 13 includes an example catheter shaft 23, and an example expandable membrane 11 that is attached to the catheter shaft 23 at a distal section 24 of the catheter shaft 23. For example, the expandable membrane 11 may be attached to the catheter shaft 23 at two locations of the catheter shaft 23 on the distal section 24 of the catheter shaft 23.

The expandable membrane 11 includes an example outer surface 25, and an example inner surface 26 that defines an interior space 27 of the expandable membrane 11. The catheter shaft 23 includes an example lumen 28 that extends from a proximal section 29 of the catheter shaft 23 to an example orifice 33 that fluidly couples the lumen 28 with the interior space 27 of the expandable membrane 11. In some examples, the expandable membrane 11 may have a thickness of about 500 microns, or not more than 500 microns. In some examples, the expandable membrane 11 may have a thickness of about 200 microns, or not more than 200 microns. In some examples, the expandable membrane 11 may have a thickness of about 100 microns, or not more than 100 microns. In some examples, the expandable membrane may have a thickness of about 50 microns, or not more than 50 microns. In some examples, the expandable membrane 11 may have a thickness in a range of 5 microns to 50 microns.

The ablation catheter 13 also includes a plurality of example electrodes 19 disposed, in this example, on the outer surface 25 of the expandable membrane 11. In this example, the plurality of electrodes 19 are arranged in a row, and may be generally circumferentially distributed around the expandable membrane 11. In the depicted example of FIG. 1, the expandable membrane 11 has been expanded, or inflated, by the fluid 22 having low electrical conductivity. In this manner, individual electrodes $19a$, $19b$, $19c$, . . . , $19i$ of the plurality of electrodes 19 may physically contact, or may come close to physically contacting, a wall of the pulmonary vein antrum tissues, or other appropriate target tissues depending on ablation target location in various implementations. Example distances between electrode centers of adjacent electrodes (e.g., between adjacent electrodes $19a$ and $19b$, between adjacent electrodes $19b$ and $19c$) may be between 2 mm and 20 mm. Any appropriate number of electrodes $19a$, $19b$, . . . , $19i$ may be included with the ablation catheter 13.

In various implementations, the fluid 22 may be a liquid or a gas, and may have low electrical conductivity. For example, the fluid 22 may have an electrical conductivity of not more than 0.01 Siemens per meter (S/m), according to various implementations. In other examples, the fluid 22 may have an electrical conductivity of between 0.00001 and 0.1 S/m. In some implementations, the fluid 22 may have the above-mentioned conductivity at room temperature (e.g., at 25 degrees Celsius). In implementations, the fluid 22 may have the above-mentioned conductivity at normal body temperature (e.g., at 37 degrees Celsius). In some examples, fluid 22 may be a dextrose solution that has low electrical conductivity, such as D5W, which is a 5% dextrose solution in water, according to some implementations. In some examples, fluid 22 may be a dextrose solution that has low electrical conductivity, such as a 10% dextrose solution in water. In some examples, fluid 22 may be a dextrose solution that has low electrical conductivity, such as a 15% dextrose solution in water. In some examples, fluid 22 may be a dextrose solution that has low electrical conductivity, such as a 20% dextrose solution in water. In some examples, fluid 22 may be a dextrose solution that has low electrical conductivity, such as a 25% dextrose solution in water. In some examples, fluid 22 may be a dextrose solution that has low electrical conductivity, such as a 30% dextrose solution in water. In some examples, fluid 22 may be a dextrose solution that has low electrical conductivity, and has a concentration of not more than 30% dextrose in water. Alternatively, fluid 22 may be deionized water in some implementations. In yet other implementations, the fluid 22 may be a gas that has low electrical conductivity, such as nitrogen, carbon dioxide, or helium, to list a few examples.

In the depicted example of FIG. 1, the fluid 22 has been passed through the lumen 28 of the catheter shaft 23 and into the interior space 27 via the orifice 33 to expand or inflate the expandable membrane 11, so as to create pressure to conform the expandable membrane 11 and its row of electrodes 19 to the anatomy of the atrial tissue, and thereby achieve good contact with the tissue. In various implementations, the fluid 22 may be injected with a syringe 30 at a port 31 of the ablation catheter 13, for example. In some examples, a pump may alternatively be used to inject the fluid 22 into the lumen 28. In some examples, the pump may be included with the generator 20, and in some examples, the pump may be a standalone pump.

In some examples, a fixed volume (or quantity) of fluid 22 may be injected into the lumen 28. A majority of the fixed volume of fluid 22 may pass through the orifice 33 and into the interior space 27 of the expandable membrane 11 to inflate the expandable membrane 11, and the fixed volume of fluid 22 may remain within the interior space 27 or lumen 28 for an entire duration, or a substantial duration, of electrical energy application by the generator 20 sufficient to fully form a desired lesion, according to some implementations. In some implementations, the fixed volume of fluid may be non-circulatory. For example, the fixed volume of fluid 22 may remain in the interior space 27 or lumen 28 for the duration of electrical energy application generally without circulating in the interior space 27. In some implementations, electrical energy application sufficient to form a desired lesion may be completed without introduction to the lumen 28 of additional fluid beyond the initially injected fixed volume of fluid 22. In some examples, the fluid 22 may be non-circulating or non-circulatory within interior space 27 for an entire duration, or a substantial duration, of electrical energy application by the generator 20 sufficient to fully form a desired lesion. In some examples, the fluid 22 may be non-circulating or non-circulatory within the system 2 for an entire duration, or a substantial duration, of electrical energy application by the generator 20 sufficient to fully form a desired lesion.

In some examples, the system 2 includes a handle 16 that can be used to manually maneuver the ablation catheter 13.

As is known generally when performing cardiac ablations with electrical energy, a goal of a pulmonary vein isolation is to create a contiguous circumferential lesion around an orifice (ostia) of the pulmonary vein, such that the lesion constitutes a barrier for any electrical activity in the pulmonary vein from conducting in the left atrium.

The plurality of electrodes 19, arranged in a row of electrodes in FIG. 1, may be used to create such a contiguous circumferential lesion, according to various implementations. In some examples, the electrodes 19 may be used to create a lesion that is not circumferential. For example, in some implementations it may be desirable to create a more local lesion that does not encompass a circumference of tissue. Examples of electrical connections to the electrodes 19 to enable electrical current to flow from the high-voltage electrical generator 20 to the electrodes 19 will be described below with reference to FIG. 3.

Figure 2:
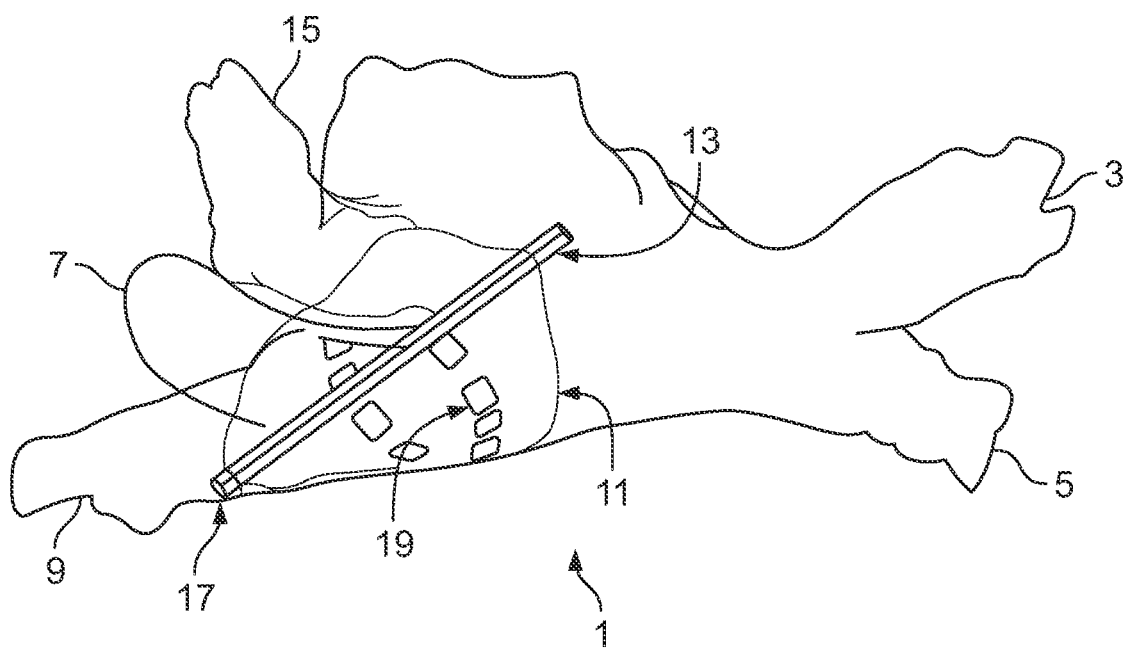
FIG. 2 is a superior view of the left atrium and a portion of the system for ablating bodily tissue of FIG. 1.

FIG. 2 shows a superior view of the left atrium 1 and a portion of the system 2 for ablating bodily tissue of FIG. 1. For simplicity, portions of the system 2 that are generally outside of the left atrium 1 are not shown in FIG. 2. It can be appreciated how the inflated expandable membrane 11 conforms to ridges and cavities of the left atrium 1 near the pulmonary veins, helping establish a good electrode contact with the walls of the left atrium 1.

Figure 3:
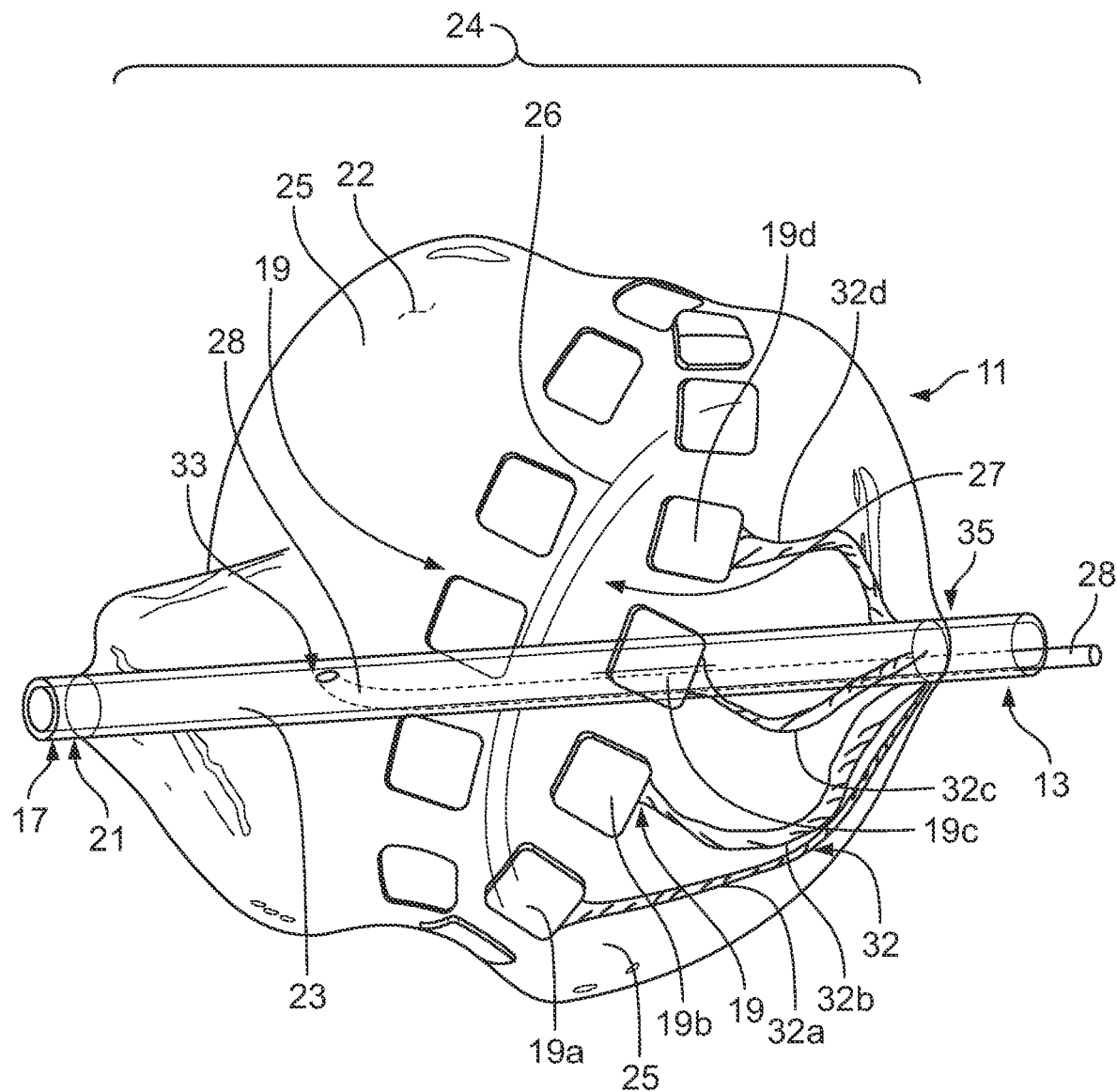
FIG. 3 is a view of a portion of the system for ablating bodily tissue of FIGS. 1 and 2.

FIG. 3 is a view of a portion of the system 2 for ablating bodily tissue of FIGS. 1 and 2. FIG. 3 shows the expandable membrane 11 with the plurality of electrodes 19 that are disposed on the outer surface 25 of the expandable membrane 11. In some examples, the electrodes 19 may include conductive metal that may be formed by deposition on a polymer of the expandable membrane 11. While the portion of the ablation catheter 13 shown in FIG. 3 is depicted outside of the left atrium for simplicity, it will be understood, based on the irregular shape of the inflated expandable membrane 11 in FIG. 3, that the expandable membrane 11 may assume such a shape as it conforms to ridges, cavities, or other surfaces of the left atrium or pulmonary veins. In some implementations, this ability to better conform to anatomical tissue that a flexible membrane may provide, as compared to a more rigid catheters that do not include a flexible membrane, may provide more efficacious lesion formation versus electroporation catheters that do not include a flexible membrane.

FIG. 3 also shows a plurality of example conductors 32, each of which may electrically couple a respective electrode with the high-voltage electrical generator 20. For example, a first conductor 32a may electrically couple the first electrode 19a with the generator 20; a second conductor 32b may electrically couple the second electrode 19b with the generator 20; a third conductor 32c may electrically couple the third electrode 19c with the generator 20; a fourth conductor 32d may electrically couple the fourth electrode 19d with the generator 20, and so on. In some examples, each conductor of the plurality of conductors 32 can include a stretchable trace of conductive metal that may be formed by deposition on a polymer of the expandable membrane 11 and a wire or flexible printed circuit that may extend from the expandable membrane 11 through the catheter shaft 23 (e.g., via a lumen of the catheter shaft), and may be electrically coupled to wires 18 (or other conductors) that are electrically coupled to the generator 20. Alternatively, in some examples the conductors 32 can be implemented by flexible printed circuits, with conductors encapsulated in an insulative polymer, which may then be disposed on the surface of the expandable membrane 11.

The conductors 32 and the electrodes 19 on the surface of the flexible membrane 11 may take various forms. In some examples, the conductors 32 and the electrodes 19 may be stretchable metal conductors. In some examples, the conductors 32 continue and may be located inside a lumen of the catheter 13, and may be electrically coupled to a generator (e.g., generator 20) by wires, for example.

In some examples, the stretchable metal conductors may be built by a spin coating of a thin film of polyimide on a sacrificial layer of poly(methylmethacrylate) can be used.

Metal evaporation, photolithography and wet etching steps can be used to define metal electrodes with, for example, serpentine-shaped interconnects (which may provide advantages in allowing the interconnects to adapt to membrane expansion) and rectangular electrodes, according to some implementations. An additional polyimide spin coating, oxygen reactive ion etching, and metal deposition for contacts may also be used. The publication "Materials for Multifunctional Balloon Catheters With Capabilities in Cardiac Electrophysiological Mapping and Ablation Therapy", by Dae-Hyeong Kim et al, Nature materials 10.4 (2011): 316-323, which is hereby incorporated by reference herein in its entirety, describes techniques for providing electrodes and conductors on a surface of a flexible membrane, and such techniques can be used to create the electrodes 19 and conductors 32, according to various implementations. In some examples, non-serpentine-shaped conductors may be used for conductors 32.

For examples where the conductors 32 may be implemented as a flexible circuit disposed on top of a balloon membrane, a thin polyimide substrate (e.g., 0.002-0.003 inches thick and a total thickness of the structure of 0.004 to 0.006 inches thick) may be used. The conductors 32 may be encapsulated in top and bottom layers of polyimide (for example, similar to circuit traces), and may terminate in exposed areas that form the ablating electrode areas. U.S. Pat. No. 9,717,557 to Salahieh et al., which is hereby incorporated by reference herein in its entirety, describes techniques for providing flexible circuits on a balloon membrane that can be used to create the electrodes 19 and conductors 32, according to various implementations.

In various implementations, the flexible circuit and multiple conductive traces can be constructed using laminations of various materials, which may include a base substrate, an electrically conductive layer and an electrically insulating layer. Multiple conductive traces can include a bottom insulating substrate layer, a middle conductive layer and a top insulating dielectric layer, according to some implementations. The dielectric or top insulating layer can be removed as is known in the art to expose a small region of the conductive layer. An adhesive layer can be used between the layers described above. The flexible circuit and associated conductive traces and conductive pads can be coupled to the balloon membrane by a variety of techniques known in the art to affix a metallic or polymer, shaped member onto another surface as are known in the art. For example, an adhesive film or other material can be used to adhere the bottom layer of the flex circuit to the balloon membrane. U.S. Pat. No. 8,295,902 to Salahieh et al., which is hereby incorporated by reference herein in its entirety, provides details on the construction of flexible circuits disposed over balloon membranes in a catheter system that can be used to create the conductors 32 and electrodes 19, according to various implementations.

Referring again to the high voltage electrical generator 20 of FIG. 1, in some examples, the generator 20 may be configured to provide electrical pulses of at least 500 volts. For example, the generator 20 may be configured to provide rectangular pulses of 500V, or at voltages larger than 500V, to the electrodes 19 of the ablation catheter 13. Pulses of other appropriate shapes may be provided in some implementations. In some examples, the generator 20 may provide pulses that are substantially rectangular, such a pulse from a discharge of a high voltage capacitor. In some examples, trapezoidal pulses may be provided. In some examples, the generator 20 may be configured to provide electrical pulses at voltages lower than 500V, such as at 400V, 300V, 200V, to list a few examples. In some examples, the generator 20 may be configured to provide pulses of at least 200V. In some examples, the generator 20 may be configured to provide pulses of at least 300V. In some examples, the generator 20 may be configured to provide pulses of at least 400V.

Figure 12:
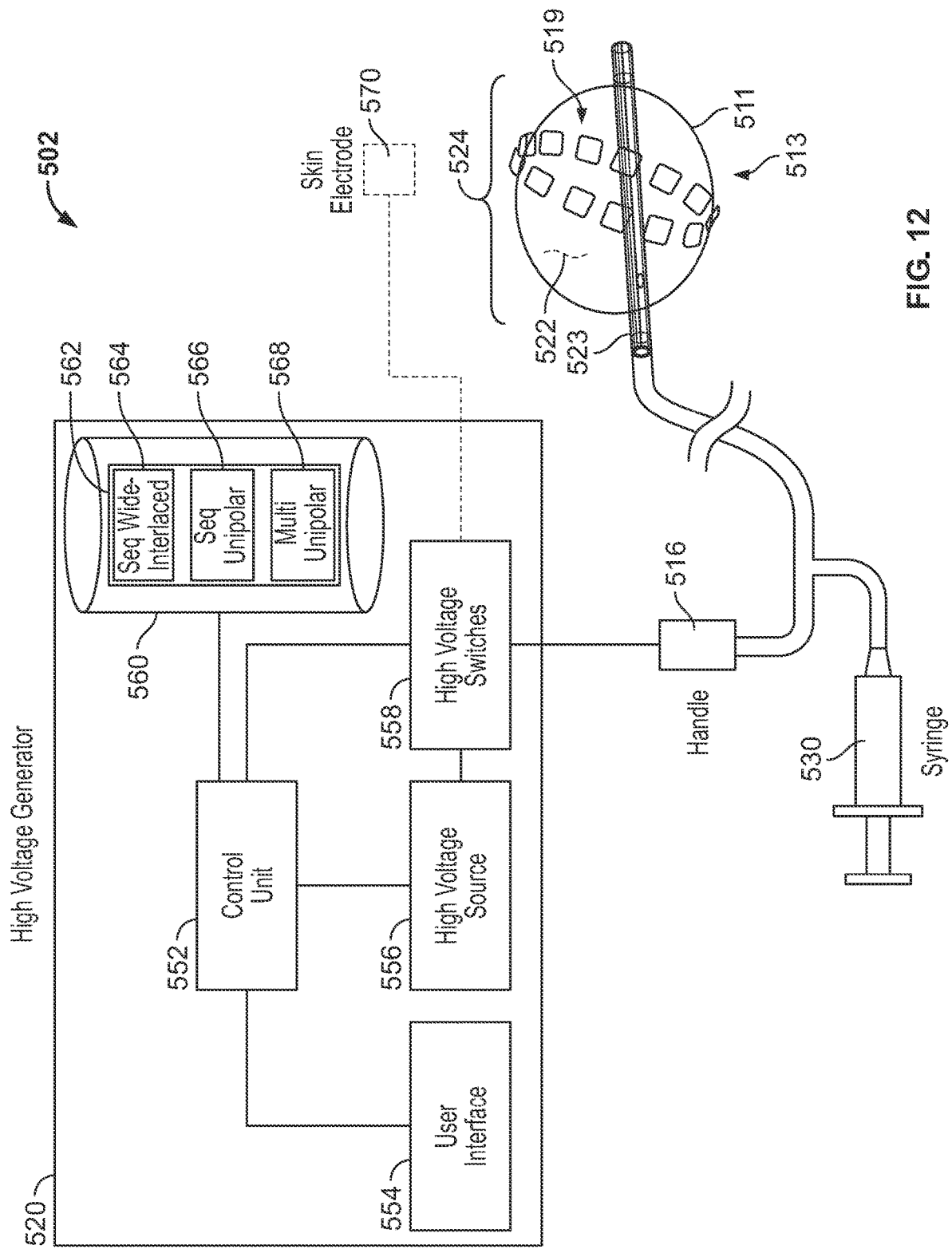
FIG. 12 is a block diagram of an example system for ablating bodily tissue.

In some examples, the pulses produced by the generator 20 may alternatively be specified based on a current level, as opposed to a voltage level, as is understood in the art of electrical engineering, for example for implementations where the generator 20 may be a current-controlled source. Examples of current levels that the generator 20 may provide, to each electrode that is sourcing electrical current, can include 2 amps (or currents of at least 2 A), 5 amps (or currents of at least 5 A), 3 amps (or currents of at least 3 A), 4 amps (or currents of at least 4 A), or 5 amps (or currents of at least 5 A), to list a few examples, according to various implementations. FIG. 12 shows a block diagram of an example electrical generator 520, which may represent generator 20 in various implementations.

The expandable membrane 11 can encapsulate a filling fluid, such as a liquid or a gas, when such fluid is injected into the system 2 for ablating bodily tissue. In some implementations, the expandable membrane 11 may be attached to the catheter shaft 23 of the ablation catheter 13 at two locations at the distal section 24 of the shaft 23. For example, the membrane 11 may be attached to the shaft 23 at a first distal location 21 at or near the distal tip 17 of the catheter shaft in the distal section 24, and at a second proximal location 35 in the distal section 24 of the shaft 23. An orifice 33 fluidly communicates the interior space 27 of the membrane with the lumen 28 of the shaft 23, such that the fluid 22, which may be injected into the lumen 28 at a port 31 outside of the patient's body, may enter the interior space 27 to inflate the expandable membrane 11. In some examples, more than one (e.g., two, three, four, or more) orifice 33 could be used to fluidly couple the interior space 27 with the lumen 28 to inflate or deflate the expandable membrane 11.

A row of electrodes 19 is shown. In this example, the row of electrodes 19 is arranged about a circumference of the expandable membrane 11, and the row of electrodes 19 may substantially reside in a plane. In other embodiments, such row may not be co-planar, for example by selecting electrodes from various circumferences. In some examples, a row of electrodes circumferentially deployed about the expandable membrane, and arranged to substantially reside in a plane, may encompass a perimeter of tissue such that, upon creation of a lesion at the locations of the tissue encompassed by the electrodes, the pulmonary vein or veins distal to the lesion may be isolated. In some examples, a row of non-co-planar electrodes may encompass a perimeter of tissue such that, upon creation of a lesion at the locations of the tissue encompassed by the electrodes, the pulmonary vein or veins distal to the lesion may be isolated.

As used herein, the term "isolating," as it pertains to the field of pulmonary vein isolation and as the term is known in the art of cardiac ablation, means that when electrodes are energized and create a sufficiently deep lesion in the tissue around a perimeter of a pulmonary vein, then the pulmonary vein may not thereafter be able to conduct electrical activity to the main part of the left atrium.

Various embodiments could include as few as three electrodes per row, or as many as 48, or more, electrodes per row. Furthermore, while a single row of electrodes has been depicted in the examples of FIGS. 1-3, in other examples more than one row of electrodes 19 (e.g., two rows, three rows, four rows, or more) could be included on the expandable membrane 11, and each row could include an appropriate number of electrodes (e.g., the same number of electrodes or a different number of electrodes) as discussed above, according to some implementations.

In the art of cardiac ablation, it is known generally that electrical impedances of electrodes can be measured to verify electrode contact to the tissue to be ablated, prior to delivery of electrical energy. Referring again to FIGS. 1-3, in some examples, electrical impedances of one or more (e.g., one, two, . . . , or all) of the electrodes in the plurality of electrodes 19 may be measured to verify electrode contact to the tissue to be ablated. In examples having more than one row of electrodes, electrode impedances may be measured for all electrodes in a particular row, according to some implementations. Based on the measurements, any one, or several, of the electrode rows, or a combination of several electrodes from such rows, that are in good contact with the tissue can be energized to create the desired perimeter lesion to the tissue, according to some implementations.

In some examples, the expandable membrane 11 may have a diameter of 15 to 40 mm when inflated with fluid 22 in ambient air, which may configure well to the dimensions of a typical human left atrium. Some embodiments have diameters of 20 to 35 mm when inflated with fluid 22 in ambient air.

FIG. 3 shows four conductors 32a, 32b, 32c, 32d, respectively electrically coupled to electrodes 19a, 19b, 19c, 19d, but it will be understood that the ablation catheter 13 may include, for each electrode of the plurality of electrodes 19, a corresponding electrical conductor 32 that electrically couples the electrode with the generator 20, such that electrical energy from the generator 20 may reach each electrode of the plurality of electrodes 19.

Figure 4A:
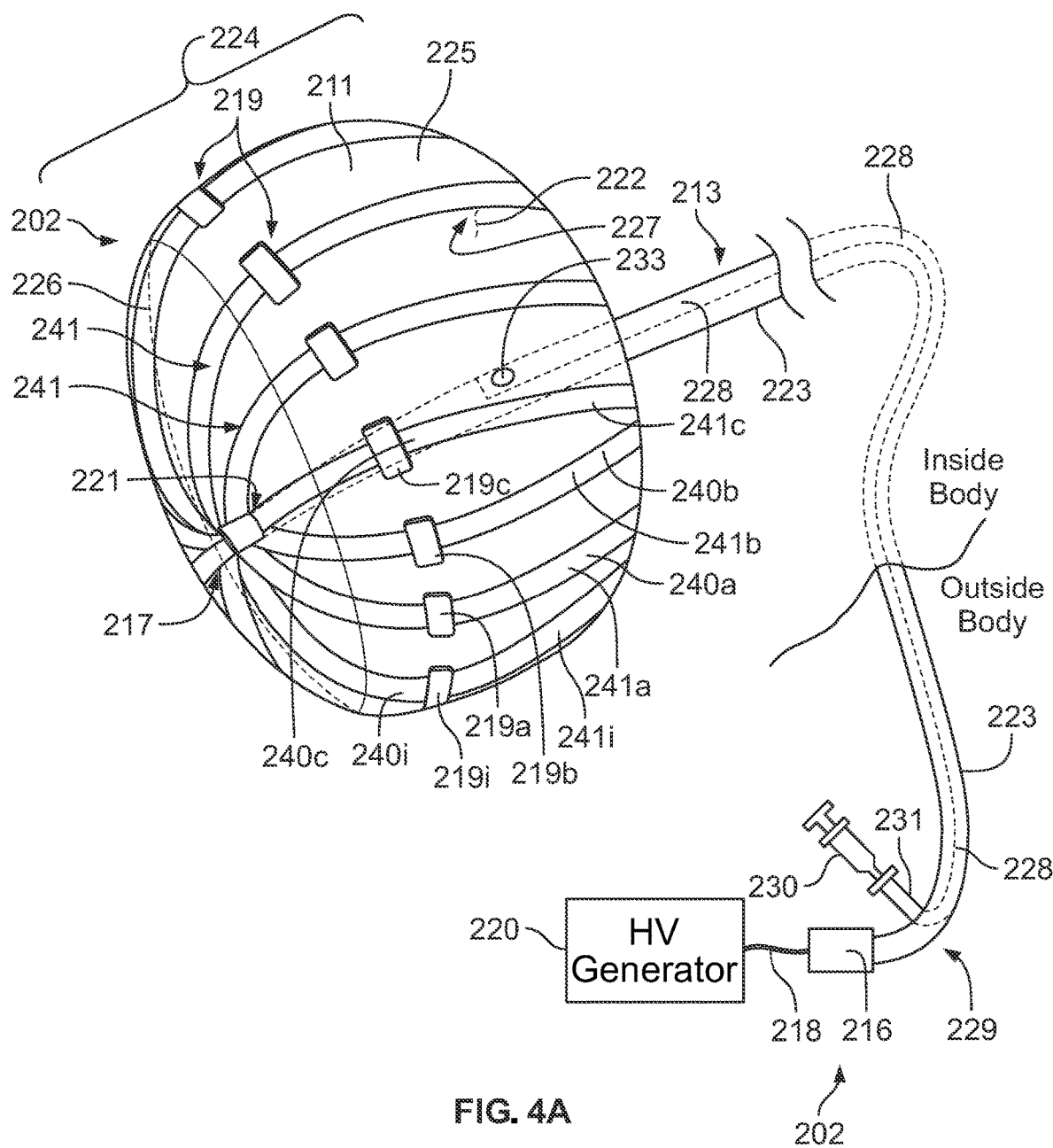
FIG. 4A is a view of another example system for ablating bodily tissue of a patient.

FIG. 4A is a view of another example system 202 for ablating bodily tissue of a patient. The system 202 for ablating bodily tissue includes an example ablation catheter 213, an example high-voltage electrical generator 220, and example fluid 222 having low electrical conductivity.

Ablation catheter 213 includes an example catheter shaft 223, and an example expandable membrane 211 that is attached to the catheter shaft 223 at a distal section 224 of the catheter shaft 223. For example, the expandable membrane 211 may be attached to the catheter shaft 223 at two locations of the catheter shaft 223 on the distal section 224 of the catheter shaft 223.

In some examples, the distal section 224 of the ablation catheter 213 may be located at an ostium of a pulmonary vein of a patient. In some examples, the distal section 224 of the ablation catheter 213 may be located at an antrum of a pulmonary vein of the patient. In some examples, the distal section 224 of the ablation catheter 213 may be located in the left atrium of the patient.

The expandable membrane 211 includes an example outer surface 225, and an example inner surface 226 that defines an interior space 227 of the expandable membrane 211. The catheter shaft 223 includes an example lumen 228 that extends from a proximal section 229 of the catheter shaft 223 to an example orifice 233 that fluidly couples the lumen 228 with the interior space 227 of the expandable membrane 211. In some examples, the expandable membrane 211 may have a thickness of about 500 microns, or not more than 500 microns. In some examples, the expandable membrane 211 may have a thickness of about 200 microns, or not more than 200 microns. In some examples, the expandable membrane 211 may have a thickness of about 100 microns, or not more than 100 microns. In some examples, the expandable membrane 211 may have a thickness of about 50 microns, or not more than 50 microns. In some examples, the expandable membrane 211 may have a thickness in a range of 5 microns to 50 microns.

The ablation catheter 213 also includes a plurality of example electrodes 219 disposed, in this example, on a plurality of example flexible splines 241, where in this example each spline includes a single electrode. For example, a first electrode 219a is disposed on an outward-facing surface 240a of a first spline 241a; a second electrode 219b is disposed on an outward-facing surface 240b of a second spline 241b; a third electrode 219c is disposed on an outward-facing surface 240c of a third spline 241c; . . . , and an i-th electrode 219i is disposed on an outward-facing surface 240i of a i-th spline 241i. Any appropriate number of splines 241 may be included with the catheter 213, and any appropriate number of electrodes (e.g., one, two, three, or more) may be included on each spline. In the depicted example of FIG. 4A, a width of the electrodes 219 is larger than a width of the splines 241, but in other examples the width of the electrodes may be smaller, or the same as, the width of the splines (for example, as depicted by the splines 341 and electrodes 319 of FIG. 4B, where the electrode width is slightly smaller than the spline width).

In some examples, the expandable membrane 211 may be inflated by the fluid 222, such that portions of the outer surface 225 of the expandable membrane 211 may contact and provide pressure against inward-facing surfaces of the flexible splines 241. In this manner, the outer surface 225 of the flexible membrane 211 may provide mechanical pressure to an underside of the flexible splines 241 so that the inflation causes the splines 241 and electrodes 219 to contact, or come close to contacting, cardiac tissue targeted for ablation, and to conform to the tissue.

In this example, the plurality of electrodes 219 are arranged in a row. In some examples, the flexible splines 241 may be flexible circuits that include electrical conductors encapsulated in a thin insulating polymer (such as polyimide, for example), with the conductors electrically connecting the electrodes 219 to the high voltage electrical generator 220, as will be described in further detail below with reference to FIG. 5.

In this example, the plurality of electrodes 219 are arranged in a row, and may be generally circumferentially distributed around the catheter 213 on the splines 241. In the depicted example of FIG. 4A, the expandable membrane 211 has been expanded, or inflated, by the fluid 222 having low electrical conductivity. In this manner, individual electrodes 219a, 219b, 219c, . . . , 219i of the plurality of electrodes 219 may physically contact, or may come close to physically contacting, a wall of the pulmonary vein antrum tissues, or other tissue targeted for ablation. Example distances between electrode centers of adjacent electrodes (e.g., between adjacent electrodes 219a and 219b, between adjacent electrodes 219b and 219c) may be between 2 mm and 20 mm. Any appropriate number of electrodes 219a, 219b, . . . , 219i may be included with the ablation catheter 213.

In various implementations, the fluid 222 may be a liquid or a gas, and may have low electrical conductivity. For example, the fluid 222 may have an electrical conductivity of not more than 0.01 Siemens per meter (S/m), according to various implementations. In other examples, the fluid 222 may have an electrical conductivity of between 0.00001 and 0.1 S/m. In some implementations, the fluid 222 may have the above-mentioned conductivity at room temperature (e.g., at 25 degrees Celsius). In implementations, the fluid 222 may have the above-mentioned conductivity at normal body temperature (e.g., at 37 degrees Celsius). In some examples, fluid 222 may be a dextrose solution that has low electrical conductivity, such as D5W, which is a 5% dextrose solution in water, according to some implementations. In some examples, fluid 222 may be a dextrose solution that has low electrical conductivity, such as a 10% dextrose solution in water. In some examples, fluid 222 may be a dextrose solution that has low electrical conductivity, such as a 15% dextrose solution in water. In some examples, fluid 222 may be a dextrose solution that has low electrical conductivity, such as a 20% dextrose solution in water. In some examples, fluid 222 may be a dextrose solution that has low electrical conductivity, such as a 25% dextrose solution in water. In some examples, fluid 222 may be a dextrose solution that has low electrical conductivity, such as a 30% dextrose solution in water. In some examples, fluid 222 may be a dextrose solution that has low electrical conductivity, and has a concentration of not more than 30% dextrose in water. Alternatively, fluid 222 may be deionized water in some implementations. In yet other implementations, the fluid 222 may be a gas that has low electrical conductivity, such as nitrogen, carbon dioxide, or helium, to list a few examples.

In the depicted example of FIG. 4A, the fluid 222 has been passed through the lumen 228 of the catheter shaft 223 and into the interior space 227 via the orifice 233 to expand or inflate the expandable membrane 211, and to provide pressure by the outer surface 225 of the membrane 211 against inward-facing surfaces of the splines 241. In some examples, the splines 241 may provide elasticity and may be distended outward by the pressure. In this manner, the electrodes 219 on the splines 241 may conform to the anatomy of the atrial tissue, and thereby achieve good contact with the tissue. In various implementations, the fluid 222 may be injected with a syringe 230 at a port 231 of the ablation catheter 213, for example. In some examples, a pump may alternatively be used to inject the fluid 222 into the lumen 228. In some examples, the pump may be included with the generator 220, and in some examples, the pump may be a standalone pump.

In some examples, a fixed volume (or quantity) of fluid 222 may be injected into the lumen 228. A majority of the fixed volume of fluid 222 may pass through the orifice 233 and into the interior space 227 of the expandable membrane 211 to inflate the expandable membrane 211, and the fixed volume of fluid 222 may remain within the interior space 227 or lumen 228 for an entire duration, or a substantial duration, of electrical energy application by the generator 220 sufficient to fully form a desired lesion, according to some implementations. In some implementations, the fixed volume of fluid may be non-circulatory. For example, the fixed volume of fluid 222 may remain in the interior space 227 or lumen 228 for the duration of electrical energy application generally without circulating in the interior space 227. In some implementations, electrical energy application sufficient to form a desired lesion may be completed without introduction to the lumen 228 of additional fluid beyond the initially injected fixed volume of fluid 222. In some examples, the fluid 222 may be non-circulating or non-circulatory within interior space 227 for an entire duration, or a substantial duration, of electrical energy application by the generator 220 sufficient to fully form a desired lesion. In some examples, the fluid 222 may be non-circulating or non-circulatory within the system 202 for an entire duration, or a substantial duration, of electrical energy application by the generator 220 sufficient to fully form a desired lesion.

In some examples, the system 202 includes a handle 216 that can be used to manually maneuver the ablation catheter 213.

The expandable membrane 211 can encapsulate a filling fluid, such as a liquid or a gas, when such fluid is injected into the system 202 for ablating bodily tissue. In some implementations, the expandable membrane 211 may be attached to the catheter shaft 223 of the ablation catheter 213 at two locations at the distal section 224 of the shaft 223. For example, the membrane 211 may be attached to the shaft 223 at a first distal location 221 at or near a distal tip 217 of the catheter shaft 223 in the distal section 224, and at a second proximal location (not shown) in the distal section 224 of the shaft 223. An orifice 233 fluidly communicates the interior space 227 of the membrane with the lumen 228 of the shaft 223, such that the fluid 222, which may be injected into the lumen 228 at a port 231 outside of the patient's body, may enter the interior space 227 to inflate the expandable membrane 211. In some examples, more than one (e.g., two, three, four, or more) orifice 233 could be used to fluidly couple the interior space 227 with the lumen 228 to inflate or deflate the expandable membrane 211.

A row of electrodes 219 is shown. In this example, the row of electrodes 219 is arranged about a circumference of the ablation catheter 213 via the splines 241, and the row of electrodes 219 may substantially reside in a plane. In other embodiments, such row may not be co-planar, for example by selecting electrodes from various circumferences. In some examples, a row of electrodes circumferentially deployed about the ablation catheter, and arranged to substantially reside in a plane, may encompass a perimeter of tissue such that, upon creation of a lesion at the locations of the tissue encompassed by the electrodes, the pulmonary vein or veins distal to the lesion may be isolated. In some examples, a row of non-co-planar electrodes may encompass a perimeter of tissue such that, upon creation of a lesion at the locations of the tissue encompassed by the electrodes, the pulmonary vein or veins distal to the lesion may be isolated.

Various embodiments could include as few as three electrodes per row, or as many as 48, or more, electrodes per row. Furthermore, while a single row of electrodes has been depicted in the example of FIG. 4A, in other examples more than one row of electrodes 219 (e.g., two rows, three rows, four rows, or more) could be included on the splines 241, and each row could include an appropriate number of electrodes (e.g., the same number of electrodes or a different number of electrodes) as discussed above, according to some implementations.

The high voltage electrical generator 220, in some examples, may be configured to provide electrical pulses of at least 500 volts. For example, the generator 220 may be configured to provide rectangular pulses of 500V, or at voltages larger than 500V, to the electrodes 219 of the ablation catheter 213. Pulses of other appropriate shapes may be provided in some implementations. In some examples, the generator 220 may provide pulses that are substantially rectangular, such a pulse from a discharge of a high voltage capacitor. In some examples, trapezoidal pulses may be provided. In some examples, the generator 220 may be configured to provide electrical pulses at voltages lower than 500V, such as at 400V, 300V, 200V, to list a few examples. In some examples, the generator 220 may be configured to provide pulses of at least 200V. In some examples, the generator 220 may be configured to provide pulses of at least 300V. In some examples, the generator 220 may be configured to provide pulses of at least 400V.

In some examples, the pulses produced by the generator 220 may alternatively be specified based on a current level, as opposed to a voltage level, as is understood in the art of electrical engineering, for example for implementations where the generator 220 may be a current-controlled source. Examples of current levels that the generator 220 may provide, to each electrode that is sourcing electrical current, can include 2 amps (or currents of at least 2 A), 3 amps (or currents of at least 3 A), 4 amps (or currents of at least 4 A), or 5 amps (or currents of at least 5 A), to list a few examples, according to various implementations. FIG. 12 shows a block diagram of an example electrical generator 520, which may represent generator 220 in various implementations.

In some examples, electrical impedances of one or more (e.g., one, two, . . . , or all) of the electrodes in the plurality of electrodes 219 may be measured to verify electrode contact to the tissue to be ablated. In examples having more than one row of electrodes, electrode impedances may be measured for all electrodes in particular row, according to some implementations. Based on the measurements, any one, or several, of the electrode rows, or a combination of several electrodes from such rows, that are in good contact with the tissue can be energized to create the desired perimeter lesion to the tissue, according to some implementations.

In some examples, the expandable membrane 211 may have a diameter of 15 to 40 mm when inflated with fluid 222 in ambient air, which may configure well to the dimensions of a typical human left atrium. Some embodiments have diameters of 20 to 35 mm when inflated with fluid 222 in ambient air.

Figure 4B:
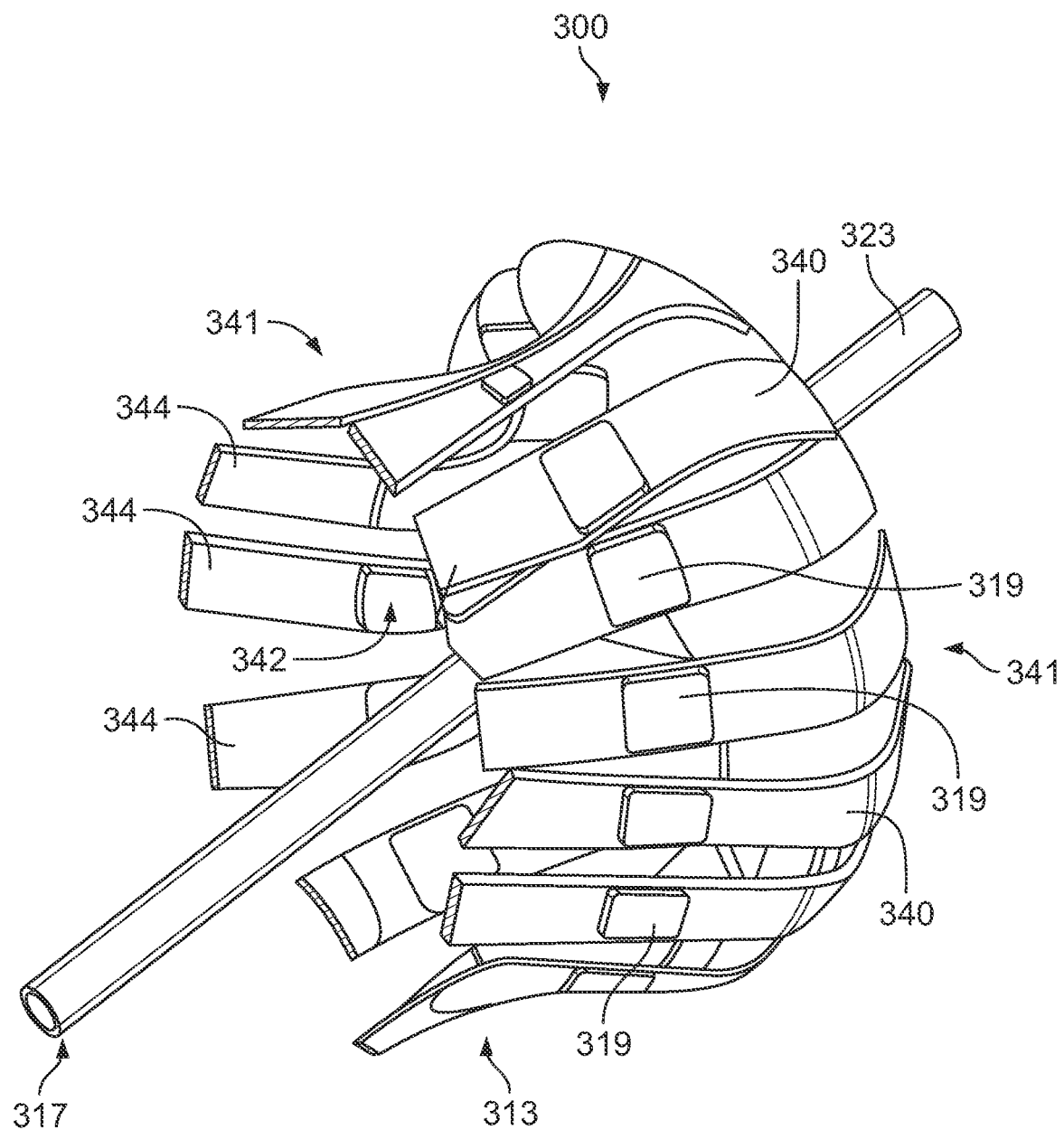
FIG. 4B is a cutaway view of a portion of an example ablation catheter.
Figure 5:
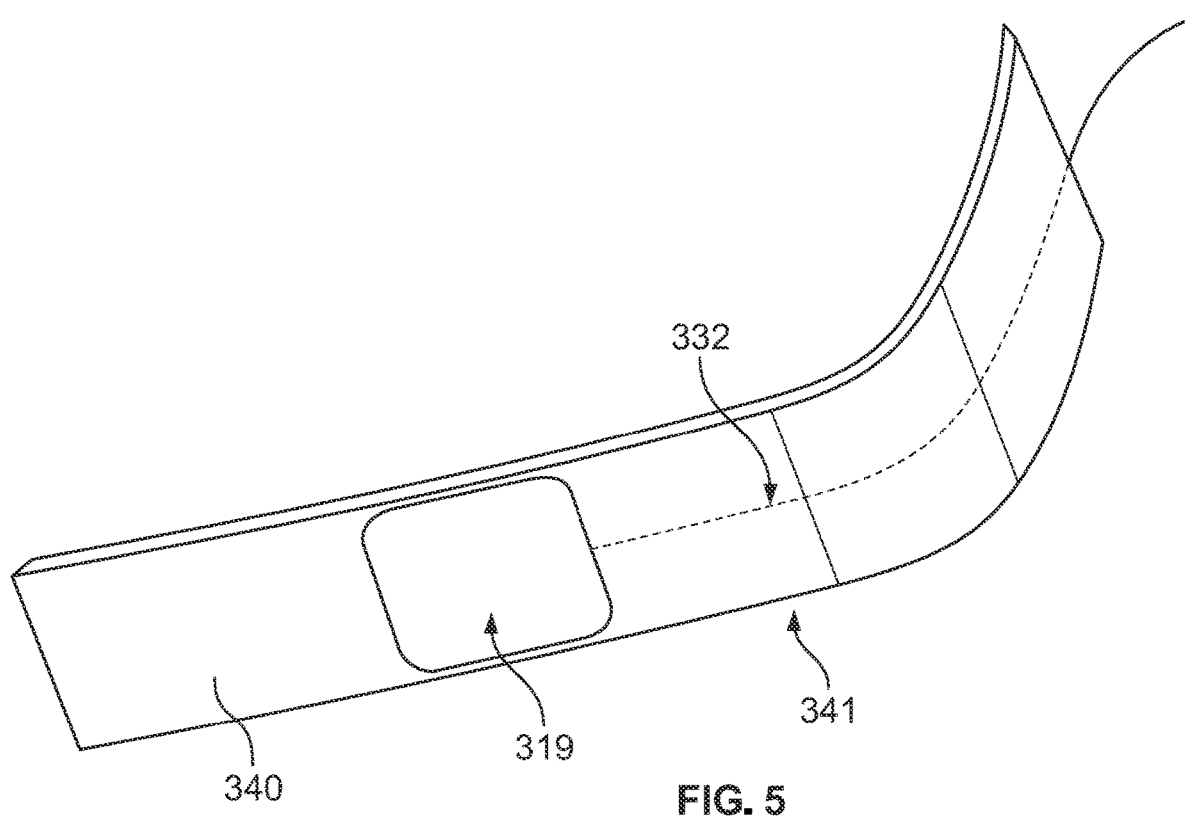
FIG. 5 is a view of a single example flexible spline of the ablation catheter of FIG. 4B.

FIG. 4B is a cutaway view of a portion 300 of an example ablation catheter 313, and FIG. 5 is a view of a single example flexible spline 341 of the ablation catheter 313 of FIG. 4B. The portion 300 of the catheter 313 includes a plurality of example flexible splines 341 that have been cut as part of the cutaway view to show example inward-facing surfaces 344 of the splines 341. Each spline of the plurality of splines 341, in the example of FIG. 4B, has an example electrode 319 disposed on an example outward-facing surface 340 of the spline 341. In this example, a width of the electrode 319 may be smaller than, or about the same as, a width of the spline 341. In other examples, the width of the electrode may be larger than the width of the spline (see, e.g., FIG. 4A).

In some examples, the splines 341 may correspond to the splines 241 of the catheter 213 of FIG. 4A. In some examples, the ablation catheter 313 may include a flexible membrane (not shown in FIG. 4B for simplicity), such as, for example, the flexible membrane 211 of FIG. 4A, and when the flexible membrane 211 may be inflated by fluid 222, the outer surface 225 of the expandable membrane 211 may contact and provide pressure against the inward-facing surfaces 344 of the flexible splines 341. In this manner, the outer surface 225 of the flexible membrane 211 may provide mechanical pressure to an underside of the flexible splines 341 so that the inflation causes the splines 341 and electrodes 319 to contact, or come close to contacting, cardiac tissue targeted for ablation, and to conform to the tissue. In some examples, the ablation catheter 313 may not include a flexible membrane.

Similar to the systems 2 and 202 of FIGS. 1 and 4A, ablation catheter 313 may be coupled to a high-voltage electrical generator (e.g., generator 220) that may provide electrical energy to energize the electrodes 319 of the catheter 313, so that tissue can be ablated. Each flexible spline 341 may be a flexible circuit, in some examples. In some examples, each flexible spline 341 may include an example electrical conductor 332 (see FIG. 5), which in some examples may be encapsulated in a thin insulating polymer (such as polyimide, for example). The conductor 332 may electrically connect the corresponding electrode 319 to an external generator (e.g., generator 220) that may generate the electrical energy for ablation via the electrodes 319. In some examples, a back side 342 of the electrode 319 may be insulated by a polymer, such as a polymer that may form a part of spline 341. This insulation on the back side 342 of the electrode 319 may help direct the current into the cardiac tissue in front of the electrode and not towards the back.

In some examples, the conductors 332 may continue and be located inside a lumen of the catheter 313, and may continue in the flexible splines 341 to reach electrodes 319. The conductors 332 may be electrically coupled to a generator (e.g., generator 220) by wires, for example.

In some examples, the catheter 313 may not include a flexible membrane, and the flexible splines 341 may provide elasticity to cause the electrodes 319 to expand towards the tissue. In some examples, the flexible splines 341 may include wires or metallic members with mechanical memory. For example, the flexible splines 341 may include metallic members that are made from materials such as Nitinol, that may effect the expansion of the splines 341 towards the tissue when the splines 341 are expanded in the heart. This expansion may occur when the catheter 313 is delivered to the heart and exits a catheter sheath (not shown), for example. Generally, catheter delivery to a desired location for ablation, and use of a catheter sheath in the delivery of general catheters is known in the art of cardiac catheterization.

The construction of the splines 341 (FIG. 4B) and 241 (FIG. 4A) may be similar to the construction of the flexible circuits as described herein above, according to various implementations. Catheters having multiple flexible splines, and without a balloon, are described in U.S. Pat. No. 10,918,438 to Weinkam et al., which is hereby incorporated by reference herein in its entirety, and such techniques can be used to construct the splines 341 of FIG. 4B in some implementations, and in some implementations can be used to construct the splines 241 of FIG. 4A. Further description of balloon catheters for ablation is given in the publication "Radiofrequency balloon devices for atrial fibrillation ablation," by Carola Gianni et al, Cardiac electrophysiology clinics 11.3 (2019): 487-493, which is hereby incorporated by reference herein in its entirety.

In the referred-to publications above, balloon catheters are described for use with radio frequency energy ablation, which conventionally relies on passing low voltage continuous electrical energy for periods of several seconds to several minutes, through the electrodes to heat the tissue and create lesions by temperature means. Lower voltages are used for RF ablation, typically less than 200 volts, when using radio frequency energy.

A faster, non-thermal method to create cardiac lesions has been developed in the last decade with the use of high voltages, by a technique called electroporation. Instead of temperature, electroporation relies on brief pulses (e.g., less than 5 milliseconds in duration, in some examples pulses of 1-200 microsecond in duration) with electrical current delivered at high voltage (for example, 200V to 3000 V, or in some examples from 300V to 3000V, or in some examples from 500V to 3000V). The resulting electrical fields damage tissue cells by irreversibly opening the pores in their cell walls.

Use of electroporation with balloon catheters is not common yet, however, since the high voltages that are used with electroporation can pose difficult dielectric withstand problems to the thin membrane of the balloon. In other words, the very thin membrane of a balloon, where balloon thicknesses for ablation catheters used for RF ablations may typically be in a range of 5 to 50 microns in thickness when inflated, can be ruptured by the high electric field caused by the high voltages used with electroporation. This risk of balloon rupture with electroporation may be particularly challenging because electrodes may be in close proximity to a membrane of balloon. It is known that electric fields are highest near edges and sharp corners of an electrode.

Referring now back to the example ablation catheters 13 and 213 of FIGS. 1 and 4A, respectively, the expandable membranes 11 and 211 may be thin enough to allow a collapsible assembly that is small enough for delivery via catheter sheath, and yet also when used with a fill fluid 22, 222 having low electrical conductivity may withstand dielectric requirements for voltages of 500V or higher as may be provided by the generators 20 and 220.

However, the thinner the membrane 11, 211, the more susceptible the membrane 11, 211 may be to electrical rupture with high voltages. As is known generally with equipment used with high voltages, thicker materials may better withstand high voltages, for example as seen with high voltage test leads used in electrical bench work, which may have thicker insulation (e.g., several mm) as compared to test leads used with lower voltages, which may have comparably thinner insulation.

Finite element computer modelling was used to test how various fluids for inflating an expandable membrane (e.g., balloon) of an ablation catheter would perform under simulated high-voltage electroporation energy delivery with an example balloon ablation catheter. For example, the modelling was used to study the electric fields across an expandable membrane (such as membrane 211) with variable membrane conductivities and variable conductivities of the fluid contained by the expandable membrane, and modeling the high voltage pulse delivery (such as the high-voltage electrical energy that may be delivered by generator 220). The variation of membrane conductivity was studied to examine effects of possible hydration or ionic permeability of a thin membrane when inside the body, and the variation in balloon fill fluid conductivity was introduced to experiment as to whether it would cause significant effects in the electric field across the membrane.

A simple model of electrodes, flexible splines, and a membrane of a balloon with a fill fluid for the balloon was constructed by the following layers in a computer model: a 25 mm deep fill fluid for the balloon, a 25 micron membrane thickness, a polyimide substrate of 100 microns on top of the membrane, an electrode metal of 50 microns depth and square with sides 3.6 mm with an area of 13 square mm, the electrode embedded in the polyimide and exposed on its top to a next layer of 2.5 mm thick myocardium (heart muscle), a layer of pericardial fluid and tissue of 300 microns, followed by 25 mm of lung and fat tissue. This stack of layers was then surrounded by a bigger sphere of tissues to simulate the rest of the body. Several of the said electrode-polyimide assemblies were spaced at 6 mm on center to simulate the splines 341 of FIG. 4B, for example. In various examples, the simulated device may generally represent the ablation catheter 213 of FIG. 4A, having flexible splines 241 and expandable membrane 211, or may generally represent a device that combines the splines 341 and electrodes 319 of FIG. 4B with the expandable membrane 211 of FIG. 4A.

With particular reference to this latter combination, the polyimide width beyond the electrode sides was 100 microns in the model. The modelled polyimide was long in the perpendicular direction, i.e., it was a rectangle of 3.8 mm width and 25 mm long, with the electrode at the center. A current of 5 amperes was modelled to pass from one of the electrodes to a simulated distant patch electrode. Appropriate conductivities found in publications were assigned to the tissues and fluids, as is conventionally done in computer modelling. Nonlinear conductivity was included for the simulated tissues since electroporation can change conductivity nonlinearly as a function of the electric field strength.

Typically, physiological saline has been used to inflate catheter balloons in hospital surgery and cardiac catheterization wards, so saline was one of the fill fluids tested using the model, given its prevalence for use as a fill fluid with balloon catheters.

One purpose of the modelling experiment was to potentially identify a less electrically conductive balloon fill fluid that might be a possible replacement fill fluid for saline. To experiment with less conductive fluids, such as less conductive liquids or gases, fill fluid options that are less conductive than saline and also safe if suddenly released into the circulation should the balloon burst were considered.

Regarding safety in an event of balloon rupture, pure water, if suddenly released into the circulation, can cause destruction of red blood cells by hemolysis. For example, a density or concentration of inner cell contents may be less than that of water, which may cause the cell to burst by osmotic pressure. Gases, if suddenly released into the circulation, can embolize (for example, can cause trapped bubbles in small vessels of the brain), and can cause ischemic stroke lesions. Also, regarding ease of use during delivery and positioning for an ablation procedure, a gas-filled balloon may tend to float in blood, and may thus make maneuvering of the catheter difficult when inside the heart's chambers, in some examples.

It was decided for the modelling experiment to simulate a 5% dextrose in water solution (278 mmol/Liter, known as "D5W"). D5W is conventionally used in intravenous fluid for hydration and nutritional support. As such, D5W may be expected to be generally safe in the circulation in the event of a balloon rupture. D5W has not conventionally been used as a catheter balloon fill fluid, however.

Figure 6:
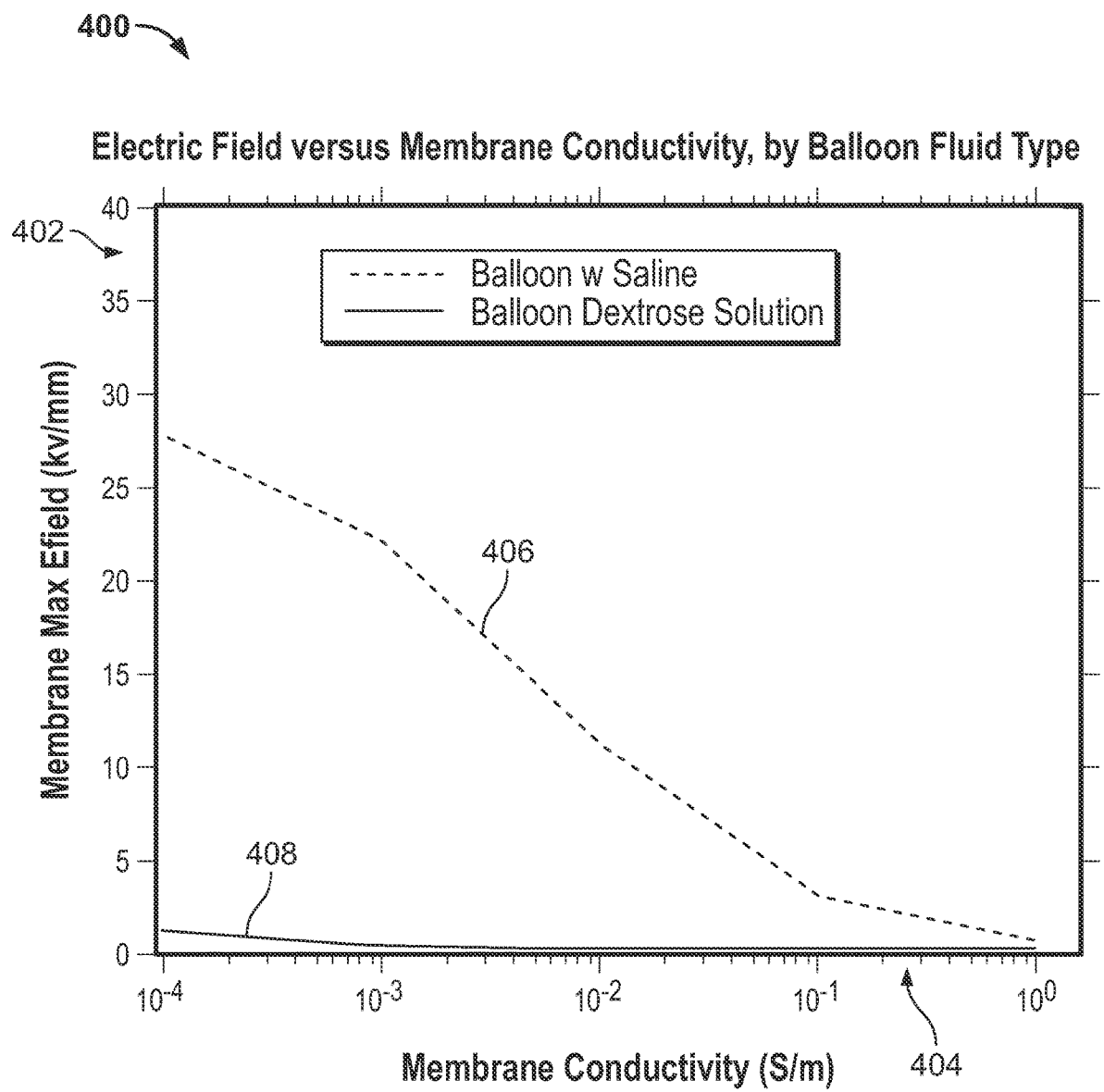
FIG. 6 is a graph that shows the results of a computer modelling of electrical field across a membrane of an ablation catheter balloon on a vertical axis versus membrane conductivity on a horizontal axis, for two different balloon-fill fluids.

FIG. 6 is a graph 400 that shows the results of a computer modelling of electrical field across a membrane of an ablation catheter balloon on a vertical axis 402 versus membrane conductivity on a horizontal axis 404, for two different balloon-fill fluids. A first curve 406 shows the simulated device using saline as a balloon-fill fluid, and a second curve 408 shows the simulated device using a dextrose solution as the balloon-fill fluid. It can be seen in the horizontal axis 404 (plotted in logarithmic scale) that the conductivity of the membrane of the balloon was varied from 0.0001 (10 to the minus 4 power) Siemens/meter to 1 Siemen per meter. In this manner, the device was simulated for a range of membrane conductivities from a relatively insulating membrane to a membrane that is relatively conductive.

With reference to the first and second curves 406 and 408, an unexpected advantage of using a 5% dextrose solution to inflate the balloon can now be appreciated. As can be seen with the first curve 406, corresponding to the modelled device with saline fill fluid, the electric field across the more insulative membrane (e.g., the membrane with conductivity 0.0001 (10 to the minus 4 power) Siemens/meter) was about 28 kV per millimeter, whereas the second curve 408, corresponding to the modelled device with dextrose solution fill fluid, the electric field across the membrane at the same membrane conductivity level was only about 1 kilovolt per mm, about 27 kV per millimeter lower than the saline fill device model.

This improved performance using the low conductivity fill fluid, such as D5W, may provide several potential advantages as compared to the traditional saline fill fluid. First, because a much lower electric field is seen at the expandable membrane with the D5W fill fluid, the expandable membrane may be much less likely to rupture. That is, an expandable membrane filled with a low-conductivity fill fluid, such as D5W, may be more resistant to electrically induced rupture. With a much-reduced likelihood of balloon rupture even at high-voltage electroporation ablation levels, use of balloon catheters for such ablations may now be possible, for example using systems such as system 2 of FIGS. 1-3, system 202 of FIG. 4A, or a system that combines aspects of system 202 and the spline 341 and electrode 319 portions of the catheter 313 of FIG. 4B.

Second, and related to the first potential advantage, using a low-conductivity fill fluid, such as D5W, may open the possibility of a wider range of elastic polymer materials for the membrane, for example those that do not require high withstand voltages, or high dielectric strength (such as 20 kV/mm or more, as seen in the experiment).

In addition, as can be seen with reference to the first and second curves 406 and 408, the largest difference in electric fields seen at the membrane occurs when the membrane conductivity is lowest (that is, more insulative, at 0.0001 Siemens per meter). This may be advantageous for catheter ablation of cardiac tissue as well, because with a membrane of a balloon (such as membrane 11 of FIGS. 1, 3, or membrane 211 of FIG. 4A) that is relatively more insulative, current delivered at the electrode may be better directed towards the tissue directly facing the electrode (the tissue intended to be ablated), and may be less directed towards the back of the electrode or into the balloon fill fluid, since the current may not easily cross the less-conductive membrane.

This combination of having a low conductivity fill fluid and a low conductivity membrane that does not rupture in the presence of high voltages may provide an advantage similar to the advantage provided by a back reflector to a light bulb (as in a flashlight), where the back reflector may help direct the bulb's radiating light forward with more efficacy, in contrast to a light bulb with no back barrier that radiates light more weakly in all directions. In a similar way, the ablation energy may be directed efficiently toward the target tissue to be ablated. With reference again to FIG. 6, advantages of the low conductivity fill fluid may still be seen at higher membrane conductivities, as can be seen by comparing the first and second curves 406 and 408 at a membrane conductivity 0.01 (10 to the minus 2 power) S/m, where the electric field across the membrane was about 11.5 kV per millimeter for the balloon with saline fill fluid, and about 0.3 kV per millimeter for the balloon with the dextrose solution fill fluid—that is, over 11 kV per millimeter lower than the saline fill device model.

Referring again to the expandable membranes 11 and 211 of FIGS. 1 and 4A, in various implementations either of those membranes may have a conductivity of not more than 0.01 S/m, for example when measured at room temperature. In some implementations, the conductivity across the membrane for membranes 11 or 211 may be not more than 0.0001 S/m, for example when measured at room temperature. In general, these relatively nonconductive membranes may help to better direct electrical current into the tissue desired to be ablated, according to some implementations.

In some examples, the expandable membranes 11, 211 described above may be made from elastic polymer materials, (for example polyurethane), and a thickness of the membrane 11, 211 may be 500 microns or less, 200 microns or less, 100 microns or less, or in some examples 50 microns or less (e.g., in a range of 5-50 microns). The results of the computer modelling indicate that when used with a low-conductivity fill fluid, the membrane 11, 211 can be more readily selected with less stringent dielectric strength values, and less thickness, even when used with the high voltages associated with electroporation, according to some implementations.

In some implementations, the ablation catheters (e.g., catheters 13, 213, 313) described herein may be configured for ablation of tissue, with electrodes (e.g., with electrodes 19, 219, 319) energized at high voltages typical of electroporation (e.g., greater than 200 Volts in some implementations, greater than 300 V in some implementations, or greater than 500 V in some implementations). In various implementations, the balloon or expandable membrane (e.g., membrane 11, 211) may include said electrodes disposed on its outer or external surface to contact the tissue. In various implementations, said electrodes may be disposed on a polymer substrate or flexible circuit spline (e.g., spline 241, 341). In some examples, the polymer substrate or flexible circuit spline may be disposed on the surface of said balloon, or may be distinct from the surface of the balloon, and may be expanded when the outer surface of the balloon pushes against an inward-facing surface of the flexible circuit spline, for example. As previously described, the balloon 11 or 211 may be filled or inflated with a fluid of 5% dextrose solution in water, or with any fluid or gas of similar or lower electrical conductivity, according to various implementations. Examples of gases that may be safe include carbon dioxide, nitrogen, and helium, according to some implementations. Examples of fluids of low conductivity can include deionized water, and any fluid with a conductivity of less than 0.01 Siemens per meter, for example.

FIGS. 1 and 2 depicted and described a balloon placed at or near left pulmonary veins, but as will be understood by those skilled in the art of catheter ablation, the devices and systems described herein may be applicable for ablation procedures at other locations as well, such as, for example ablations at or near the right pulmonary veins, or to other anatomical locations in the heart, such as the right atrium, the right ventricle, left ventricle, or even epicardial approaches where the electrodes are applied to the epicardial walls of the heart.

In this latter epicardial wall example, an embodiment catheter may be configured to be delivered percutaneously via a sub-xiphoid approach to within a pericardial space, and may include a balloon that inflates to a flattened volume when deployed and inflated in the pericardial space. Such flattened balloon, which may resemble a small pancake in shape, may have electrodes disposed on its surface so as to contact the epicardial wall. This embodiment may be suitable, for example for ventricular tissue ablation, for the treatment of ventricular arrhythmia.

Figure 7:
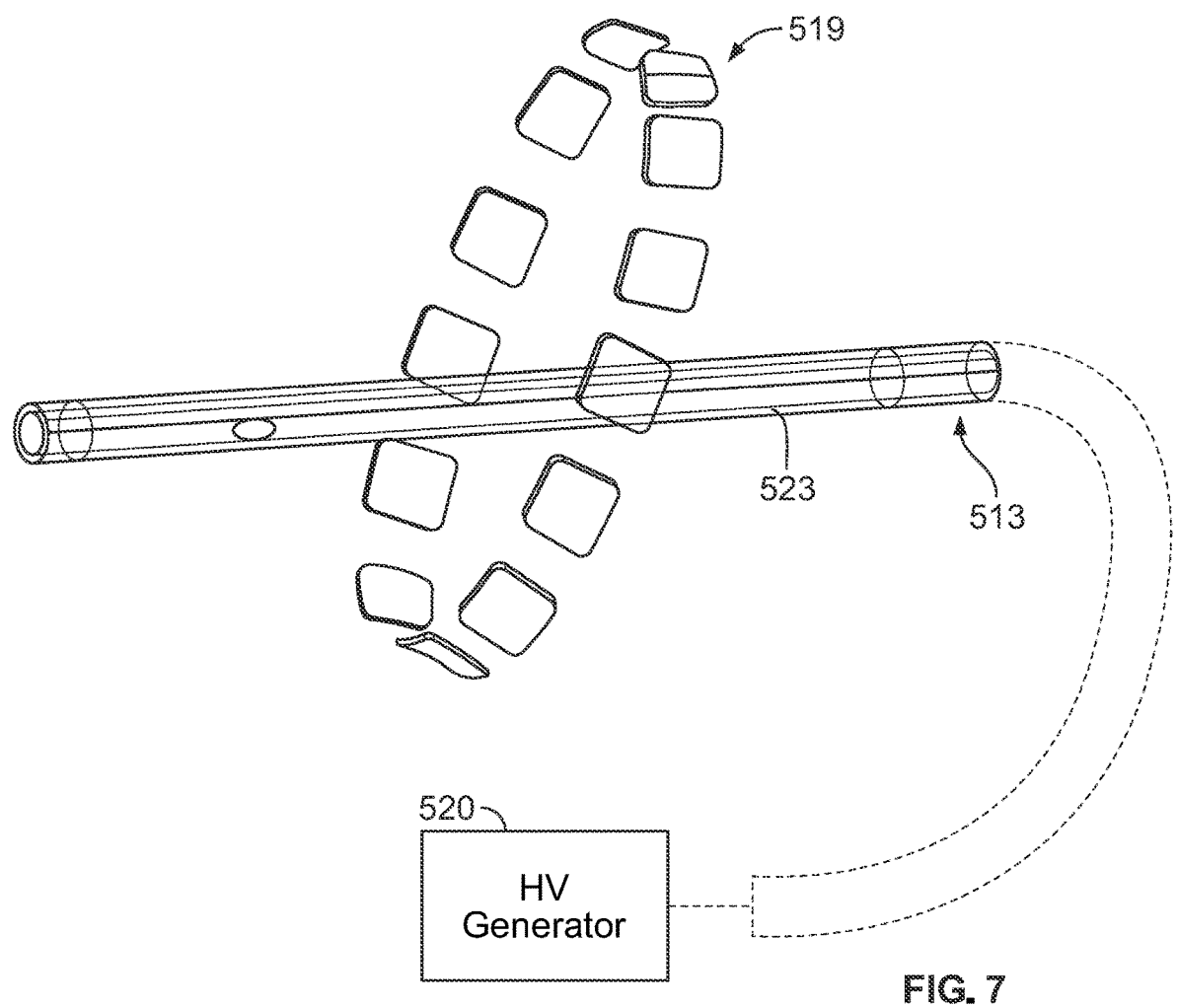
FIG. 7 is a view of a portion of an example system for ablating bodily tissue.

FIG. 7 is a view of a portion of an example system for ablating bodily tissue. FIG. 7 shows an example ablation catheter 513 that includes a generic catheter shaft 523 and example electrodes 519 arranged as a ring. FIG. 7 may simplistically represent, for the purposes of the following discussion, either an example portion of a balloon ablation catheter for use in a system for ablation (such as the system 2 of FIGS. 1-3, for example), or an example portion of an ablation catheter with splines that also includes a balloon for use in a system for ablation (such as the system 202 of FIG. 4A, for example), or an example portion of an ablation catheter with splines that does not include a balloon for use in a system for ablation (such as the system described with reference to FIG. 4B, for examples where that portion of the catheter does not include a balloon).

The question addressed by the following is: what are different ways to energize the electrodes so that the target tissue is efficaciously and completely treated with a therapeutic lesion, while using the least amount of electrical current possible? Also desired, from a safety perspective, is a delivery of electrical current via the electrodes so as to minimize the amount of electrical energy in tissues that are not being targeted in a cardiac ablation.

Also shown in FIG. 7 is an example high-voltage electrical generator 520 that may include a sequential, wide-interlaced delivery algorithm, and this will be further described below with reference to FIGS. 8, 9A, 9C and 9D, following a discussion of some known electroporation energy delivery methods.

One known method to deliver electroporation energy to the heart, which has been used with catheter shafts that include ring electrodes (but which do not include a balloon), involves sourcing electrical current simultaneously from all the catheter electrodes to a patch electrode on the back of the patient. That is, each of the electrodes on the catheter act as an electrical source, and the patch electrode on the patient's back acts as an electrical sink. This method is referred to as "multiple unipolar," or "multi-unipolar" in this document.

Another known method, which will be referred to as the "interlaced energy delivery method" herein, which has been used with catheters that include rigid, linear ringed electrodes on a shaft of the catheter (but which do not include a balloon), alternates current sources with current sinks (ground) among the electrodes. To be clear, and describing this method in terms of voltage, positive and negative voltages (polarities) are applied with this method in an alternating fashion to the electrodes. For example, if the electrodes are numbered sequentially, all of the odd-numbered electrodes are energized as current sources with positive polarity, and all the even-numbered electrodes are treated as current sinks. The interlaced energy delivery method has been used for radio frequency energy ablation and electroporation ablation with catheters that include rigid, linear ringed electrodes on a shaft of the catheter (but which do not include a balloon), and has an advantage of keeping the current very close to the electrodes, and away from extra-cardiac vulnerable tissues, such as the esophagus.

Figure 10:
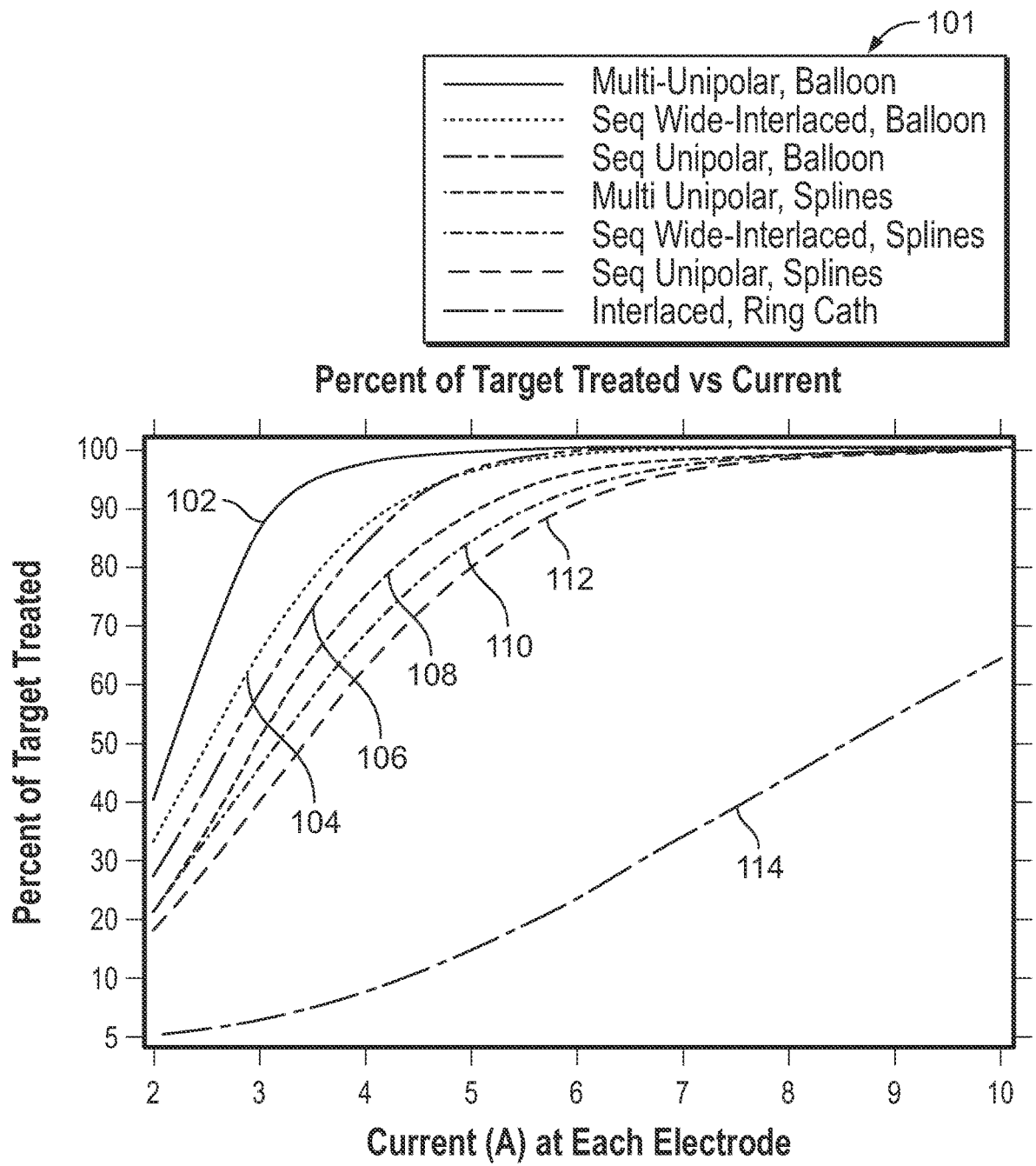
FIG. 10 is a graph showing results of a computer modelling experiment comparing the efficacy of various catheter energy delivery configurations.
Figure 11:
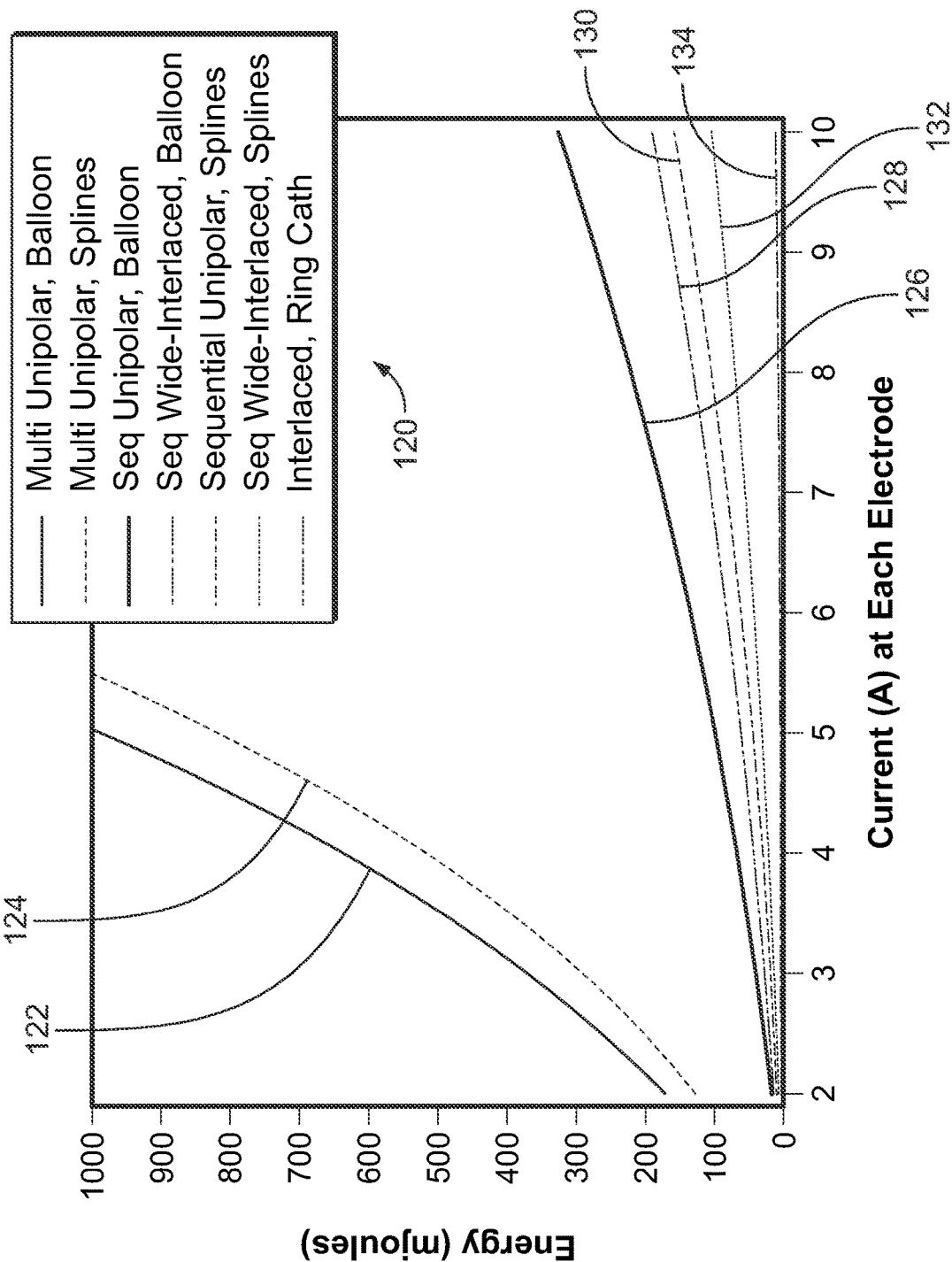
FIG. 11 is a graph showing results of a computer modelling experiment comparing the safety of various catheter energy delivery configurations.

However, computer modeling experiments, which will be explained in more detail below and with reference to FIGS. 10 and 11, show that while this interlaced energy delivery method may be generally a safe method (meaning little current excursion outside the heart tissues), this interlaced energy delivery method may be less efficacious, and may be inefficient when the intent is to treat the full thickness of the myocardial target. Also, the interlaced method may create very high electric fields between the electrodes. With the higher voltages of electroporation (as described previously above), these fields will be even higher (as compared to fields produced with RF ablation systems) and may cause arcing and gas formation at those areas.

Also, in some implementations, the interlaced energy delivery method may be difficult to use with electrodes that are not mounted on a relatively rigid catheter. For example, if the interlaced energy delivery method were to be used with a traditional elastic balloon catheter, or with a traditional catheter with splines that is less rigid, in some implementations there might be an increased risk of a short circuit or arcing between adjacent electrodes, for example because the adjacent electrodes, which are of opposite polarity with the interlaced delivery method, may come close to one another due to anatomy of the ablation location, for example. By contrast, the more rigid ring electrode catheter may better maintain the electrodes at fixed distances from each other, and may minimize a risk of short circuits or arcing that may occur with the traditional flexible spline catheters or traditional balloon catheters.

The interlaced energy delivery method has historically been limited for implementation only with relatively rigid linear ring catheters, where the electrodes are on the shaft of the catheter, so that distances between adjacent electrodes may be maintained for adequate separation to prevent short circuits. This limitation of rigidity has prevented the use of the interlaced delivery method with catheters that include balloon membranes or flexible polymer splines that provide back insulation so as to direct electrical current exclusively towards the front of the electrode and into the targeted tissue.

Therefore, a method of energy delivery that has the benefits of keeping electric currents relatively close to the heart and away from vulnerable tissues (e.g., the esophagus) but does not have a high risk of short circuits with adjacent electrodes, and can take advantage of a back insulation, whether it is provided by a balloon membrane catheter (e.g., the catheter of FIG. 3) or by a polymer of a flexible spline catheter (e.g., the catheters of FIGS. 4A, 4B), is desired. Described now will be a new method of energy delivery, which will be referred to as the sequential wide-interlaced delivery method, as well as experiments that were used to test this method.

Figure 8:
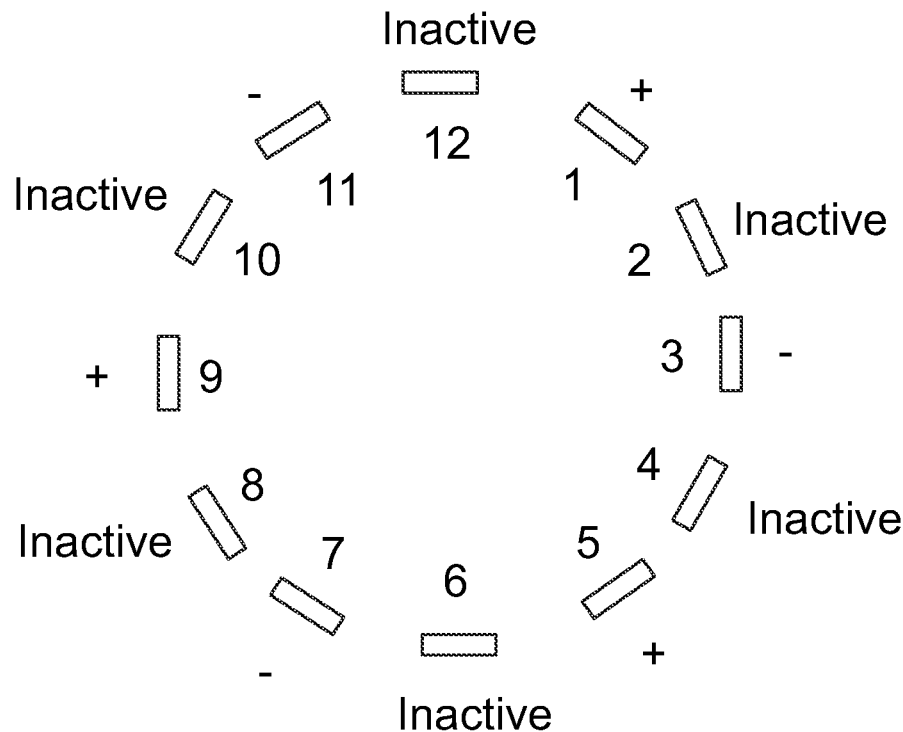
FIG. 8 is a schematic that shows an example energy delivery method for ablating bodily tissue.
Figure 8:
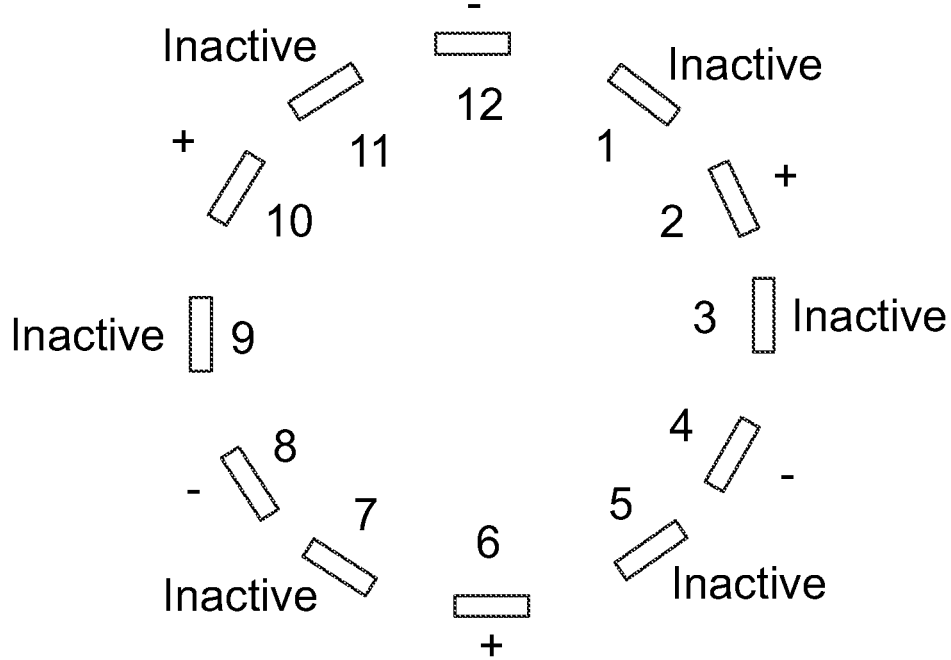

FIG. 8 is a schematic that shows an example energy delivery method for ablating bodily tissue. The energy delivery method of FIG. 8, which will be referred to as a sequential wide-interlaced delivery method herein, includes a first energy delivery 81 and a second energy delivery 82. While the sequential wide-interlaced delivery method may generally be used with any appropriate number of electrodes, the example of FIG. 8 uses twelve electrodes. FIG. 8 shows schematically a sequential wide-interlaced method of delivery for an example implementation of any of the systems for ablating tissue discussed herein, such as system 2, system 202, and the system discussed with reference to FIG. 4B, and includes twelve electrodes. The view of FIG. 8 is a frontal view of a plane approximately containing the electrodes 519 of FIG. 7, and may be used to ablate a perimeter of tissue. Currents may be delivered in two sequential steps 81, 82 in this embodiment. For example, the first energy delivery 81 may include energizing every fourth electrode with a positive voltage starting with electrode 1 (that is, electrodes 1, 5 and 9 in this example), and similarly applying negative voltages to every fourth electrode starting with electrode 3 (that is, electrodes 3, 7 and 11 in this example). Electrodes to which neither the positive voltage nor the negative voltage is applied (that is, electrodes 2, 4, 6, 8, 10 and 12) may be inactive. The foregoing can be seen with reference to delivery 81 of FIG. 8, where electrodes 1, 5 and 9 are labelled with a "+" symbol, electrodes 3, 7 and 11 are labelled with a "−" symbol, and electrodes 2, 4, 6, 8, 10 and 12 are labelled "Inactive." In this manner, there may always be an inactive electrode between electrodes of opposite polarity, which may help in preventing arcing or short circuits.

The second energy delivery 82 may be delivered after the first energy delivery 81. As depicted in FIG. 8, the second energy delivery 82 may include energizing every fourth electrode with a positive voltage starting with electrode 2 (that is, electrodes 2, 6 and 10 in this example), and similarly applying negative voltages to every fourth electrode starting with electrode 4 (that is, electrodes 4, 8 and 12 in this example). Electrodes to which neither the positive voltage nor the negative voltage is applied (that is, electrodes 1, 3, 5, 7, 9 and 11) may be inactive. The foregoing can be seen with reference to delivery 82 of FIG. 8, where electrodes 2, 6 and 10 are labelled with a "+" symbol, electrodes 4, 8 and 12 are labelled with a "−" symbol, and electrodes 1, 3, 5, 7, 9 and 11 are labelled "Inactive." Here, with the second energy delivery 82, the polarities indicated in the first energy delivery 81 are shifted by one electrode. By inactive, or non-energized, it is meant that the electrode is placed in a high impedance state. For example, in a state that is non-energized, inactive, disconnected or floating, as is known in the electrical engineering arts when referring to an electrode inactive state.

Durations for first energy delivery 81 and for second energy delivery 82 can be of various durations, according to various implementations. For example, the energy deliveries 81, 82 can be of a duration of about 100 microseconds (or less than 100 microseconds) in some implementations. In some implementations, the energy deliveries 81, 82 can be of a duration of about 10 milliseconds (or less than 10 milliseconds). In some implementations, the energy deliveries 81, 82 can be of a duration of about 10 microseconds (or less than 10 microseconds). In some implementations, pulses as described may be delivered repeatedly, in trains of pulses that may have a duration in the range of 0.1 seconds to 5 seconds (for example, pulse train durations of 0.1 s, 0.5 s, 1.0 s, 1.5 s, 2.0 s, 2.5 s, 3.0 s, 3.5 s, 4.0 s, 4.5 s, or 5.0 s, in various implementations).

The depicted energy delivery method of FIG. 8 may include sequential application of energy delivery 81 and energy delivery 82, each of which may always maintain inactive electrodes between and adjacent to electrodes that are sinking or sourcing current, without regard to which energy delivery 81 or energy delivery 82 is applied first in temporal order. Also, each of energy delivery 81 and energy delivery 82 may be applied one after the other, permitting current to be either sinked or sourced at all electrodes over time due to the alternating nature of the deliveries 81, 82, which may permit better lesion formation, according to some implementations.

In some embodiments, the polarity positive or negative may refer to the polarity of the first phase pulse of a biphasic or multiphasic waveform used for effecting electroporation.

Figures 9A, 9B, 9C, 9D:
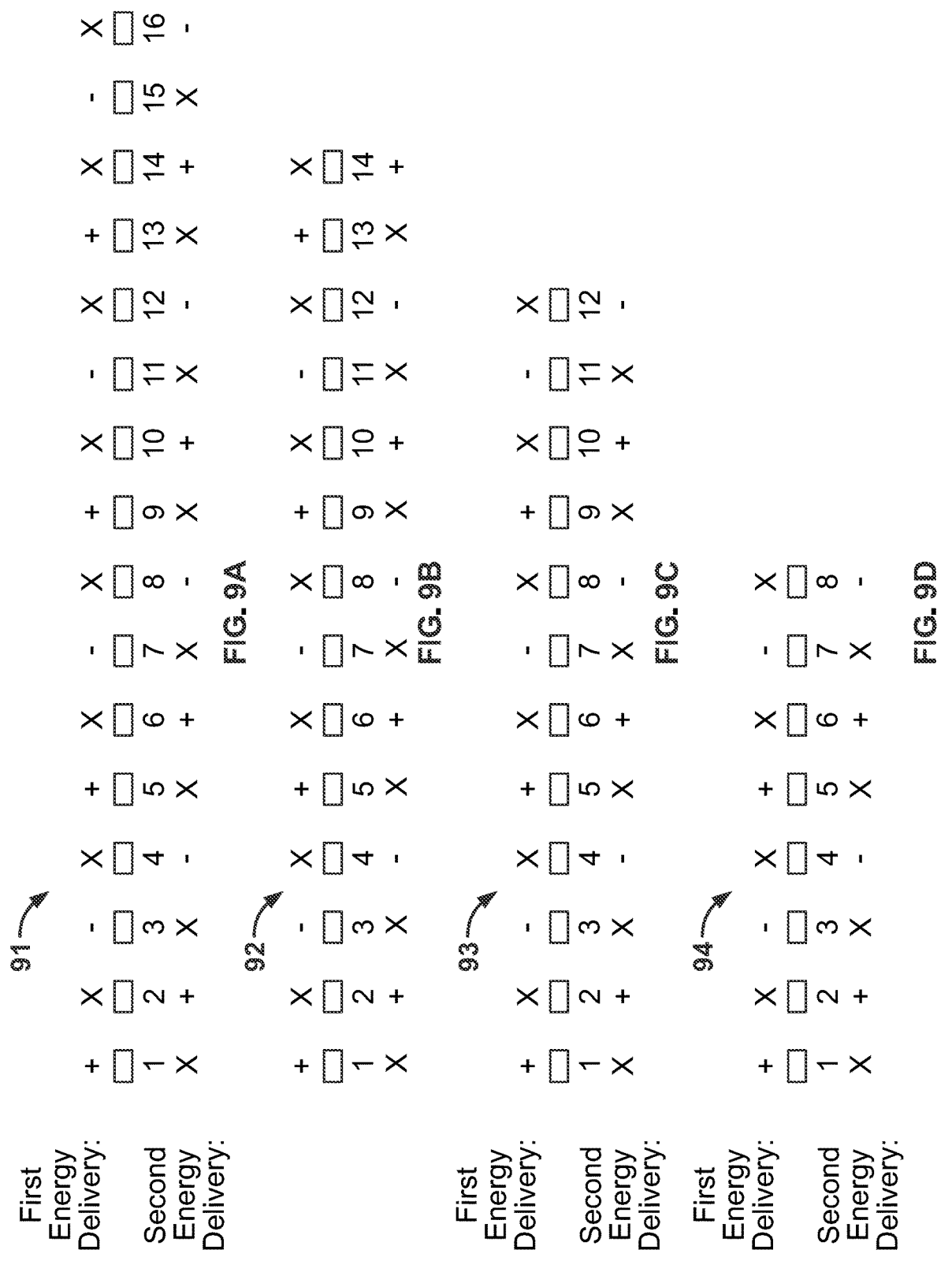

Returning now to the discussion of the sequential wide-interlaced energy delivery method discussed above with reference to FIG. 8, FIG. 9A is a schematic that shows an example energy delivery method 91 for ablating bodily tissue, for an example system with sixteen electrodes. FIG. 9A depicts an extension of the sequential wide-interlaced method of FIG. 8, as it may be applied to a 16-electrode example, where the electrodes are numbered 1-16. Similar to the first and second energy deliveries 81, 82 of FIG. 8, FIG. 9A shows a first energy delivery, indicated by the symbols above the electrodes 1-16, and a second energy delivery, indicated by the symbols below the electrodes 1-16, in a flattened single depiction rather than the two circular depictions of FIG. 8. In FIG. 9A, the first energy delivery applies a positive polarity to each of electrodes 1, 5, 9, and 13, as indicated by the "+" symbol above these electrodes, applies a negative polarity to each of electrodes 3, 7, 11 and 15, as indicated by the "−" symbol above these electrodes, and holds each of electrodes 2, 4, 6, 8, 10, 12, 14 and 16 inactive, as indicated by the "X" symbol above these electrodes. In FIG. 9A, the second energy delivery applies a positive polarity to each of electrodes 2, 6, 10, and 14, as indicated by the "+" symbol below these electrodes, applies a negative polarity to each of electrodes 4, 8, 12 and 16, as indicated by the "−" symbol below these electrodes, and holds each of electrodes 1, 3, 5, 7, 9, 11, 13 and 15 inactive, as indicated by the "X" symbol below these electrodes.

Similar to FIG. 9A, FIG. 9C is a schematic that shows another example energy delivery method 93 for ablating bodily tissue, for an example system with twelve electrodes, and FIG. 9D is a schematic that shows yet another example energy delivery method 94 for ablating bodily tissue, for an example system with eight electrodes. Each of methods 93 and 94 include a respective first energy delivery step, where polarities for each electrode are depicted above the corresponding electrode, and a respective second energy delivery step, where polarities for each electrode are depicted below the corresponding electrode.

Each of the sequential wide interlaced energy delivery methods described above with reference to FIGS. 8, 9A, 9C and 9D included a multiple of electrodes that is divisible by four (e.g., FIGS. 8 and 9C have twelve electrodes; FIG. 9A has sixteen electrodes, and FIG. 9D has eight electrodes). In various implementations, the techniques described with reference to these FIGS. 8, 9A, 9C, 9D may be extended to any appropriate number of electrodes. For example, such techniques may be extended to systems having 20 electrodes, 24 electrodes, 28 electrodes, 32 electrodes, or more).

In some examples, the sequential wide-interlaced energy delivery method may be used with systems that include a number of electrodes that is not divisible by four. While in some examples, the sequential wide-interlaced energy delivery method may work most efficiently with systems that include a number of electrodes that is divisible by four, as will described next with reference to FIG. 9B, the sequential wide-interlaced energy delivery method may nevertheless be effectively used with any appropriate number of electrodes, including those with a number of electrodes that is not divisible by four, according to various implementations.

FIG. 9B is a schematic that shows another example energy delivery method 92 for ablating bodily tissue, for a system with 14 electrodes. FIG. 9B shows how a sequential wide-interlaced energy delivery 92 may be applied for a 14-electrode row. The method 92 includes a first energy delivery, corresponding to the symbols above the electrodes, and a second energy delivery, corresponding to the symbols below the electrodes. In this example, because electrode 1 and electrode 13 in the first energy delivery (symbols above the electrodes) are both energized positively without having a negatively energized electrode between them (e.g., only inactive electrode 14 is between them locally), electrodes 1 and 13 form a contiguous region where only positively charged or inactive electrodes are present. In some examples, this arrangement may imply that current may be weaker in the vicinity of intervening electrode 14, as compared to implementations of the sequential wide-interlaced energy delivery method that use a number of electrodes that is divisible by four. A similar effect occurs in the second energy delivery (symbols below the electrodes), where current may be weaker in the vicinity of electrode 1 due its simultaneously positive neighboring electrodes 2 and 14. As such, application of the sequential wide-interlaced energy delivery method may perform better when a number of electrodes involved in the two sequential energy deliveries are a multiple of four, but may still be effective for numbers of electrodes that are not a multiple of 4.

It will be understood that in some embodiments the sequential wide-interlaced delivery can be accomplished with a voltage-controlled source applying a similar positive voltage to all the positive electrodes connected together, and a similar negative voltage to all the negative electrodes connected together, with positive and negative electrodes understood as denoted in FIGS. 8 and 9A-9D.

Alternatively, some embodiments may employ current-controlled sources that apply the same magnitude source currents to each of the positive source electrodes, for example those electrodes labelled "+" (positive) in FIGS. 8 and 9A-9D, while connecting the ground sink to all of the electrodes labeled "−" (negative) in FIGS. 8 and 9A-9D.

In some implementations, positive polarity may mean a positive voltage with respect to a ground of the circuit, or with respect to the negative electrodes. In some implementations, positive polarity may also mean a current source applied to the corresponding electrode. In some implementations, negative polarity may mean a ground voltage or a voltage lower than the positive voltage, both with respect to ground of the circuit. In some implementations, negative polarity may mean a current sink applied to the corresponding electrode.

Similar to the computer modelling discussed above with reference to FIG. 6, additional modelling and simulation was performed to test various electrical energy distribution methods, including the sequential, wide-interlaced method described above, for various configurations. With this model, a detailed and realistic anatomical model of the left atrium and surrounding organs was used. Simulated as part of the modelling experiment was a model of the FIG. 1 system 2 for ablating tissue, including a balloon ablation catheter having electrodes disposed on an outer surface of the flexible membrane of the balloon, such as the catheter 13 of FIG. 1. Also simulated was a model of the catheter 313 of FIG. 4B, including an ablation catheter having electrodes disposed on flexible splines.

Various electrode configurations for energy delivery were simulated, using various energy delivery methods. These included:
a) Multi-unipolar, balloon. This model uses a balloon ablation catheter, and an energy delivery method where all electrodes on the balloon catheter are energized to source the same amount of current simultaneously. The current sink is modeled as a patch electrode located in the back of the patient. This energy delivery method of energizing all electrodes to source current with a patch electrode as a sink has not been used with a balloon ablation catheter. The multi-unipolar energy delivery method has been used with circular catheters that do not include a balloon, however.
b) Sequential unipolar, balloon. This model uses a balloon ablation catheter, and an energy delivery method where the electrodes on the balloon catheter are energized one at a time, sequentially, each sourcing the same amount of current in turn. The current sink is modeled as a patch electrode located in the back of the patient. This energy delivery method of energizing electrodes sequentially to source current with a patch electrode as a sink has not been used for high-voltage electroporation ablation with a balloon ablation catheter.
c) Multi-unipolar, splines. This model uses an ablation catheter with flexible splines, and an energy delivery method where all electrodes on the spline catheter are energized to source the same amount of current simultaneously. The current sink is modelled as a patch electrode located in the back of the patient. This energy delivery method of energizing all electrodes to source current with a patch electrode as a sink has been used with circular ablation catheters that do not include flexible splines.
d) Sequential unipolar, splines. This model uses an ablation catheter with flexible splines, and an energy delivery method where the electrodes on the splines are energized one at a time, sequentially, each sourcing the same amount of current in turn. The current sink is modeled as a patch electrode located in the back of the patient. This delivery method of energizing electrodes on splines sequentially to source current with a patch electrode as a sink has not been used for high-voltage electroporation ablation with an ablation catheter with flexible splines.
e) Interlaced, ringed catheter. This model uses a conventional semi-rigid catheter with ring electrodes on the catheter, and a conventional energy delivery method where, for a sequentially numbered set of the ring electrodes, all odd-numbered ring electrodes are energized with a first polarity (e.g., positive polarity), and all even-numbered ring electrodes are simultaneously energized with the opposite polarity (e.g., negative polarity).
f) Sequential wide interlaced, balloon. This model uses a balloon ablation catheter, and an energy delivery method where the electrodes on the balloon catheter are energized in two sequential energy deliveries, as described above with reference to FIG. 8. The model uses an example catheter embodiment with twelve electrodes.
g) Sequential wide interlaced, splines. This model uses an ablation catheter with flexible splines, and an energy delivery method where electrodes on the splines are energized in two sequential energy deliveries, as described above with reference to FIG. 8. The model uses an example catheter embodiment with twelve electrodes.

An ablation target was defined in the computer model as a 6 mm wide volume of left atrial wall at the antrum (entrance) of the left pulmonary veins. The target was centered in front of the electrodes, the wall being 2 mm in thickness in the computer model. The target volume was approximately 60 mm in length, wrapping around only the posterior aspect of the left atrial wall. The volume of the target was 569 cubic millimeters in the computer model.

In the experiment, the measure of efficacy of electroporation was defined as the percentage of volume of target tissue that had more than 600 Volts per cm in electric field strength, (for example, a definition of "treated" or electroporated tissue for the experiment). This measure of efficacy was measured as a function current sourced at the source electrodes of each of the tested configurations. For example, for a sourcing current of 3 Amperes in the modelling experiment, the "multi-unipolar" configurations modelled all electrodes of the catheter as sourcing 3 Amperes each. As a second example, with the "interlaced" configurations, all positive (source) electrodes each sourced 3 Amperes. A higher percentage of treated target tissue is therefore desirable, such that an effective therapeutic lesion may be created.

As a measure of safety, energy dissipated in the esophagus and aorta was measured, where these are tissues just outside of the left atrium near the left pulmonary veins, and tissues where energy exposure is not desired because such exposure may damage these tissues. To model the high-voltage pulses used with electroporation ablation, a 100-microsecond pulse was delivered to the modelled source electrodes. It is desirable that said power dissipation be as small as possible, to avoid injuring the non-cardiac tissues, yet still sufficient to create the therapeutic lesion at the target tissue. Overall, one desires a high efficacy and a high safety profile for a given energy delivery configuration.

FIG. 10 is a graph showing results of a computer modelling experiment comparing the efficacy of various catheter energy delivery configurations, showing efficacy results of the modelling experiments. A legend 101 lists the configurations tested in the modelling experiment. The curves can be identified from the legend 101: the order of the configurations from top to bottom is the same order of the graphed curves 102-114 from top to bottom. For example, a top curve 102 corresponds to the "Multi-Unipolar, balloon" configuration, described above; a second curve 104 corresponds to the "Sequential Wide-Interlaced, balloon" configuration, described above; a third curve 106 corresponds to the "Sequential Unipolar, balloon" configuration, described above; a fourth curve 108 corresponds to the "Multi-Unipolar, splines" configuration, described above; a fifth curve 110 corresponds to the "Sequential Wide-Interlaced, splines" configuration, described above; a sixth curve 112 corresponds to the "Sequential Unipolar, splines" configuration, described above; and a bottom curve 114 corresponds to the "Interlaced Ring Catheter" configuration, described above. Furthermore, the curves 102, 104, 106 signify configurations with a balloon, the curves 108, 110, 112 signify flexible spline configurations, and the curve 114 corresponds to the ring catheter configuration.

Referring to FIG. 10, it can be appreciated that the Multi-Unipolar balloon configuration 102 had the highest performance versus current, achieving nearly 100% efficacy with approximately 4 Amperes. All of the simulated balloon configurations, represented by curves 102, 104, 106, performed better than the simulated splined configurations, represented by curves 108, 110, 112 or ring catheter configuration 114.

FIG. 11 is a graph showing results of a computer modelling experiment comparing the safety of various catheter energy delivery configurations, showing safety results of the modelling experiments. As with the graph of FIG. 10, the order of the curves from top-to-bottom in FIG. 11 follows the same order as the listings in a legend 120. For example, a first curve 122 corresponds to the "Multi-Unipolar, balloon" configuration; a second curve 124 corresponds to the "Multi-Unipolar, splines" configuration; a third curve 126 corresponds to the "Sequential Unipolar, balloon" configuration; a fourth curve 128 corresponds to the "Sequential Wide-Interlaced, balloon" configuration; a fifth curve 130 corresponds to the "Sequential Unipolar, splines" configuration; a sixth curve 132 corresponds to the "Sequential Wide-Interlaced, splines" configuration; and a seventh curve 134 corresponds to the "Interlaced Ring Catheter" configuration.

With reference to FIG. 11, it can be seen that the multi-unipolar systems, represented by curves 122 and 124, are very expensive in terms of safety: the energy delivered to the esophagus and the aorta quickly escalates with increasing current, which may indicate a heightened risk of tissue damage for these sensitive tissues that are near the target area for ablation in the computer model.

Combined, the computer modelling results for efficacy (FIG. 10) and safety (FIG. 11) may demonstrate advantages in both efficacy and safety of the wide-interlaced systems (which are represented by curves 104 and 110 in FIG. 10, and by curves 128 and 132 in FIG. 11), according to some implementations. If one discounts the multi-unipolar configurations due to their inferior safety profile (see FIG. 11), the inventive sequential wide-interlaced configurations may offer advantages from an efficacy and safety compromise perspective, according to various implementations.

Some implementations of the devices, systems, and methods discussed herein may include a balloon catheter (FIGS. 1-3) or a catheter with splines (FIG. 4A, which includes a balloon, and FIG. 4B which may or may not include a balloon) that can deliver energy with the sequential wide-interlaced method described above.

FIG. 12 is a block diagram of an example system 502 for ablating bodily tissue. The system 502 includes an example ablation catheter 513, an example high-voltage electrical generator 520, and example fluid 522 having low electrical conductivity.

The ablation catheter 513 may represent any of the example ablation catheters discussed herein, in various implementations. For example, the ablation catheter 513 may represent any of the ablation catheters discussed above with reference to FIG. 1, 2, 3, 4A, 4B, or 5. In the example of FIG. 12, the ablation catheter 513 includes an example catheter shaft 523, and an example expandable membrane 511 that is attached to the catheter shaft 523 at a distal section 524 of the catheter shaft 523. The example fluid 522, which is located within an interior space defined by the expandable membrane 511, may be injected into the system 502 via an example syringe 530, in a similar manner as discussed herein above. An example handle 516 may be used to maneuver the ablation catheter 513. The ablation catheter 513 also includes a plurality of example electrodes 519. An optional skin electrode 570, which may be attached for example to a back of a patient, is also shown in FIG. 12.

The example high-voltage generator 520 can include an example control unit 552, an example user interface 554, an example high-voltage source 556, example high-voltage switches 558, and an example data store 560, according to various implementations. The control unit 552 may include one or more microcontrollers, microprocessors, or digital signal processors, in some examples, and may execute instructions stored in data store 560 to perform tasks for the generator 520, according to some implementations. The user interface 554 may include, according to various implementations, one or more input devices (e.g., keyboard, buttons, touchscreen, mouse, and the like) and one or more output devices (e.g., display, which in some implementations may be a touchscreen, LED's, a speaker for providing audible feedback, and the like) that a user may use to provide input to, or receive output from, the generator 520. The high-voltage source 556 may include, according to various implementations, one or more high-voltage transformers, one or more high-voltage capacitors, or a combination of the foregoing, which may be used to provide high-voltage energy for use by the ablation catheter 513. For example, the high-voltage source 556 may provide electrical pulses of at least 500V, or other appropriate voltages, as discussed herein above with respect to the example generators 20, 220. The high-voltage switches 558 may include, according to various implementations, high-voltage insulated gate bipolar transistors (IGBT) or similar switches that may connect the high voltage source 556 to the electrodes 519 of the ablation catheter 513 (via conductors that may pass through the catheter shaft 523 and to the electrodes 519, as discussed herein above), and optionally to the optional skin electrode 570 for implementations that may use the skin electrode 570.

The data store 560 may store a collection 562 of energy delivery methods, which in the depicted example includes an example sequential, wide-interlaced energy delivery method 564, an example sequential unipolar energy delivery method 566, and an example multi-unipolar energy delivery method 568, each of which may include instructions that represent the corresponding energy delivery method, and which may be executed by the control unit 552, according to various implementations.

The sequential, wide-interlaced energy delivery method 564 has been described herein above with reference to FIGS. 8, 9A, 9C, and 9D for implementations that use a number of electrodes divisible by four, and generally with reference to FIG. 9B for implementations that do not use a number of electrodes that is divisible by four. The sequential unipolar energy delivery method 566 and the multi-unipolar energy delivery method 568 also have been described herein above.

In general, electronic circuits or components such as those represented by the high voltage source 556 and the high voltage switches 558 in FIG. 12 have long been known to those skilled in the art of electrical and electronics engineering. For example, a publication describing the construction, circuits and materials to build a high voltage signal generator for electroporation is given by a thesis entitled "High Voltage Signal Generator for Biomedical Applications" by Jonathan M. Tse, published by the University of Canterbury, Christchurch, New Zealand, in November of 2011. Another publication describing how to build a high voltage generator and switching circuits is "Design of an Irreversible Electroporation System for Clinical Use", by Bertachinni et al, Technology in cancer research & treatment 6.4 (2007): 313-320. Both of these publications are herein incorporated by reference in their entirety.

In various implementations, the control unit 552 may control the high voltage source 556 and the high voltage switches 558, for example using the any of the example energy delivery methods 564, 566, and 568, to deliver high voltage or high current electrical energy to the electrodes 519.

The above description provides examples of some implementations. Other implementations that are not explicitly described above are also possible, such as implementations based on modifications and/or variations of the features described above. For example, the techniques described above may be implemented in different orders, with the inclusion of one or more additional steps, and/or with the exclusion of one or more of the identified steps. Similarly, the devices, systems and methods described herein may include one or more additional features, may exclude one or more of the identified features, and/or include the identified features combined in a different way than presented above. Features that are described as singular may be implemented as a plurality of such features. Likewise, features that are described as a plurality may be implemented as singular instances of such features. The drawings are intended to be illustrative and may not precisely depict some implementations. Variations in sizing, placement, shapes, angles, curvatures, and/or the positioning of features relative to each other are possible. Accordingly, other implementations are within the scope of the following claims.

What is claimed is:

1. A system for performing electroporation ablation, comprising:
   a catheter that includes a plurality of electrodes, wherein the plurality of electrodes comprises a number of electrodes that is at least 8, and wherein the number of electrodes is evenly divisible by 4;
   an electrical generator comprising a plurality of current sources, each current source of the plurality of current sources adapted to provide current pulses at a voltage of at least 500 volts;
   a plurality of switches coupled to the electrical generator, and coupled to the plurality of electrodes via a plurality of electrical conductors; and
   a control unit adapted to provide an energy delivery sequence to the plurality of electrodes via the electrical generator, the plurality of switches, and the plurality of electrical conductors, wherein the energy delivery sequence includes a first energy delivery and a second energy delivery;
   wherein the control unit is adapted to configure a first energy delivery configuration, that includes:
      beginning with a first electrode of the plurality of electrodes, the first electrode and every fourth electrode thereafter of the plurality of electrodes to be an electrode having positive polarity;
      beginning with a second electrode of the plurality of electrodes, the second electrode and every second electrode thereafter of the plurality of electrodes to be inactive, wherein the second electrode is adjacent to the first electrode; and
      beginning with a third electrode of the plurality of electrodes, the third electrode and every fourth electrode thereafter of the plurality of electrodes to be an electrode having negative polarity, wherein the third electrode is adjacent to the second electrode, and wherein the second electrode is between the first electrode and the third electrode; and
   wherein the control unit is adapted to cause each of the electrodes of the first energy delivery configuration having negative polarity to be electrically connected together, is adapted to couple each of the electrodes of the first energy delivery configuration having positive polarity to a respective current source of the plurality of current sources, and is adapted to cause the electrical generator to deliver the first energy delivery by causing each of the current sources coupled to an electrode of the first energy delivery configuration having positive polarity to provide current pulses at a voltage of at least 500 volts, wherein electrical current from the provided current pulses flows from the electrodes of the first energy delivery configuration having positive polarity to the electrodes of the first energy delivery configuration having negative polarity; and
   wherein the control unit is adapted to configure a second energy delivery configuration, that includes:
      beginning with the second electrode of the plurality of electrodes, the second electrode and every fourth electrode thereafter of the plurality of electrodes to be an electrode having positive polarity;
      beginning with the third electrode of the plurality of electrodes, the third electrode and every second electrode thereafter of the plurality of electrodes to be inactive, wherein the third electrode is adjacent to the second electrode; and
      beginning with a fourth electrode of the plurality of electrodes, the fourth electrode and every fourth electrode thereafter of the plurality of electrodes to be an electrode having negative polarity, wherein the fourth electrode is adjacent to the third electrode, and wherein the third electrode is between the second electrode and the fourth electrode; and wherein the control unit is adapted to cause each of the electrodes of the second energy delivery configuration having negative polarity to be electrically connected together, is adapted to couple each of the electrodes of the second energy delivery configuration having positive polarity to a respective current source of the plurality of current sources, and is adapted to cause the electrical generator to deliver the second energy delivery by causing each of the current sources coupled to an electrode of the second energy delivery configuration having positive polarity to provide current pulses at a voltage of at least 500 volts, wherein electrical current from the provided current pulses flows from the electrodes of the second energy delivery configuration having positive polarity to the electrodes of the second energy delivery configuration having negative polarity.

2. The system of claim 1, wherein the catheter is a balloon catheter.

3. The system of claim 2, wherein the balloon catheter includes a balloon membrane, and wherein the plurality of electrodes are disposed on an outer surface of the balloon membrane.

4. The system of claim 2, wherein the catheter includes a plurality of flexible splines, and wherein each electrode of the plurality of electrodes is respectively disposed on a flexible spline of the plurality of flexible splines.

5. The system of claim 1, wherein the catheter includes a plurality of flexible splines, and wherein each electrode of the plurality of electrodes is respectively disposed on a flexible spline of the plurality of flexible splines.

6. The system of claim 1, wherein the electrodes of the plurality of electrodes substantially reside in a plane.

7. The system of claim 1, wherein the electrodes of the plurality of electrodes are non-coplanar.

8. The system of claim 1, wherein the first energy delivery comprises a series of pulses.

9. The system of claim 1, wherein the control unit is adapted to cause the electrical generator to deliver the first energy delivery, and to subsequently cause the electrical generator to deliver the second energy delivery.

10. The system of claim 1, wherein the control unit is adapted to cause the electrical generator to deliver the second energy delivery, and to subsequently cause the electrical generator to deliver the first energy delivery.

11. The system of claim 1, wherein a distal portion of the catheter is located at at least one of an ostium of a pulmonary vein of a patient, at an antrum of a pulmonary vein of the patient, or at a left atrium of the patient.

12. A system for performing electroporation ablation, comprising:
 a catheter that includes eight electrodes;
 an electrical generator comprising a plurality of current sources, each current source of the plurality of current sources adapted to provide current pulses at a voltage of at least 500 volts;
 a plurality of switches coupled to the electrical generator, and coupled to the electrodes via a plurality of electrical conductors; and
 a control unit adapted to provide an energy delivery sequence to the electrodes via the electrical generator, the plurality of switches, and the plurality of electrical conductors, wherein the energy delivery sequence includes a first energy delivery and a second energy delivery;
 wherein the control unit is adapted to configure a first energy delivery configuration, that includes:
  a first electrode of the eight electrodes to be an electrode having positive polarity;
  a second electrode of the eight electrodes to be inactive, wherein the second electrode is adjacent the first electrode;
  a third electrode of the eight electrodes to be an electrode having negative polarity, wherein the third electrode is adjacent the second electrode;
  a fourth electrode of the eight electrodes to be inactive, wherein the fourth electrode is adjacent the third electrode;
  a fifth electrode of the eight electrodes to be an electrode having positive polarity, wherein the fifth electrode is adjacent the fourth electrode;
  a sixth electrode of the eight electrodes to be inactive, wherein the sixth electrode is adjacent the fifth electrode;
  a seventh electrode of the eight electrodes to be an electrode having negative polarity, wherein the seventh electrode is adjacent the sixth electrode;
  an eighth electrode of the eight electrodes to be inactive, wherein the eighth electrode is adjacent the seventh electrode; and
 wherein the control unit is adapted to cause each of the electrodes of the first energy delivery configuration having negative polarity to be electrically connected together, is adapted to couple each of the electrodes of the first energy delivery configuration having positive polarity to a respective current source of the plurality of current sources, and is adapted to cause the electrical generator to deliver the first energy delivery by causing each of the current sources coupled to an electrode of the first energy delivery configuration having positive polarity to provide current pulses at a voltage of at least 500 volts, wherein electrical current from the provided current pulses flows from the electrodes of the first energy delivery configuration having positive polarity to the electrodes of the first energy delivery configuration having negative polarity; and
 wherein the control unit is adapted to configure a second energy delivery configuration, that includes:
  the first electrode of the eight electrodes to be inactive;
  the second electrode of the eight electrodes to be an electrode having positive polarity, the third electrode of the eight electrodes to be inactive;
  the fourth electrode of the eight electrodes to be an electrode having negative polarity;
  the fifth electrode of the eight electrodes to be inactive;
  the sixth electrode of the eight electrodes to be an electrode having positive polarity;
  the seventh electrode of the eight electrodes to be inactive;
  the eighth electrode of the eight electrodes to be an electrode having negative polarity; and
 wherein the control unit is adapted to cause each of the electrodes of the second energy delivery configuration having negative polarity to be electrically connected together, is adapted to couple each of the electrodes of the second energy delivery configuration having positive polarity to a respective current source of the plurality of current sources, and is adapted to cause the electrical generator to deliver the second energy delivery by causing each of the current sources coupled to an electrode of the second energy delivery configuration having positive polarity to provide current pulses at a voltage of at least 500 volts, wherein electrical current from the provided current pulses flows from the electrodes of the second energy delivery configuration having positive polarity to the electrodes of the second energy delivery configuration having negative polarity.

13. A system for performing electroporation ablation, comprising:
a catheter that includes twelve electrodes;
an electrical generator comprising a plurality of current sources, each current source of the plurality of current sources adapted to provide current pulses at a voltage of at least 500 volts;
a plurality of switches coupled to the electrical generator, and coupled to the electrodes via a plurality of electrical conductors; and
a control unit adapted to provide an energy delivery sequence to the electrodes via the electrical generator, the plurality of switches, and the plurality of electrical conductors, wherein the energy delivery sequence includes a first energy delivery and a second energy delivery;
wherein the control unit is adapted to configure a first energy delivery configuration, that includes:
a first electrode of the twelve electrodes to be an electrode having positive polarity;
a second electrode of the twelve electrodes to be inactive, wherein the second electrode is adjacent the first electrode;
a third electrode of the twelve electrodes to be an electrode having negative polarity, wherein the third electrode is adjacent the second electrode;
a fourth electrode of the twelve electrodes to be inactive, wherein the fourth electrode is adjacent the third electrode;
a fifth electrode of the twelve electrodes to be an electrode having positive polarity, wherein the fifth electrode is adjacent the fourth electrode;
a sixth electrode of the twelve electrodes to be inactive, wherein the sixth electrode is adjacent the fifth electrode;
a seventh electrode of the twelve electrodes to be an electrode having negative polarity, wherein the seventh electrode is adjacent the sixth electrode;
an eighth electrode of the twelve electrodes to be inactive, wherein the eighth electrode is adjacent the seventh electrode;
a ninth electrode of the twelve electrodes to be an electrode having positive polarity, wherein the ninth electrode is adjacent the eighth electrode;
a tenth electrode of the twelve electrodes to be inactive, wherein the tenth electrode is adjacent the ninth electrode;
an eleventh electrode of the twelve electrodes to be an electrode having negative polarity, wherein the eleventh electrode is adjacent the tenth electrode;
a twelfth electrode of the twelve electrodes to be inactive, wherein the twelfth electrode is adjacent the eleventh electrode; and
wherein the control unit is adapted to cause each of the electrodes of the first energy delivery configuration having negative polarity to be electrically connected together, is adapted to couple each of the electrodes of the first energy delivery configuration having positive polarity to a respective current source of the plurality of current sources, and is adapted to cause the electrical generator to deliver the first energy delivery by causing each of the current sources coupled to an electrode of the first energy delivery configuration having positive polarity to provide current pulses at a voltage of at least 500 volts, wherein electrical current from the provided current pulses flows from the electrodes of the first energy delivery configuration having positive polarity to the electrodes of the first energy delivery configuration having negative polarity; and
wherein the control unit is adapted to configure a second energy delivery configuration, that includes:
the first electrode of the twelve electrodes to be inactive;
the second electrode of the twelve electrodes to be an electrode having positive polarity;
the third electrode of the twelve electrodes to be inactive;
the fourth electrode of the twelve electrodes to be an electrode having negative polarity;
the fifth electrode of the twelve electrodes to be inactive;
the sixth electrode of the twelve electrodes to be an electrode having positive polarity;
the seventh electrode of the twelve electrodes to be inactive;
the eighth electrode of the twelve electrodes to be an electrode having negative polarity;
the ninth electrode of the twelve electrodes to be inactive;
the tenth electrode of the twelve electrodes to be an electrode having positive polarity;
the eleventh electrode of the twelve electrodes to be inactive;
the twelfth electrode of the twelve electrodes to be an electrode having negative polarity; and
wherein the control unit is adapted to cause each of the electrodes of the second energy delivery configuration having negative polarity to be electrically connected together, is adapted to couple each of the electrodes of the second energy delivery configuration having positive polarity to a respective current source of the plurality of current sources, and is adapted to cause the electrical generator to deliver the second energy delivery by causing each of the current sources coupled to an electrode of the second energy delivery configuration having positive polarity to provide current pulses at a voltage of at least 500 volts, wherein electrical current from the provided current pulses flows from the electrodes of the second energy delivery configuration having positive polarity to the electrodes of the second energy delivery configuration having negative polarity.

14. The system of claim 1, wherein each of the current pulses of the first energy delivery have a same magnitude.

15. The system of claim 1, wherein each of the current pulses of the second energy delivery have a same magnitude.

16. The system of claim 1, wherein each of the current pulses of the first energy delivery and each of the current pulses of the second energy delivery have a same magnitude.

* * * * *